(12) United States Patent
Tomazic et al.

(10) Patent No.: US 6,514,965 B1
(45) Date of Patent: Feb. 4, 2003

(54) SUBSTITUTED 1-BENZAZEPINES AND DERIVATIVES THEREOF

(75) Inventors: Alenka Tomazic, Gaithersburg, MD (US); Liren Huang, Rockville, MD (US); Kenneth D. Tucker, Frederick, MD (US)

(73) Assignee: Antex Pharma Inc., Gaithersburg, MD (US)

( * ) Notice: Subject to any disclaimer, the term of this patent is extended or adjusted under 35 U.S.C. 154(b) by 0 days.

(21) Appl. No.: 09/706,863

(22) Filed: Nov. 7, 2000

Related U.S. Application Data

(60) Provisional application No. 60/166,167, filed on Nov. 18, 1999.

(51) Int. Cl.[7] .................. C07D 487/00; C07D 491/00; C07D 498/00; C07D 513/00; A61K 31/55
(52) U.S. Cl. .................................. 514/212.07; 540/523
(58) Field of Search ................. 514/212.07; 540/523

(56) References Cited

U.S. PATENT DOCUMENTS

| | | | |
|---|---|---|---|
| 3,509,130 A | * 4/1970 | Bencze | 260/239 |
| 4,885,364 A | 12/1989 | Thottathil | 540/523 |
| 5,106,851 A | * 4/1992 | Turconi et al. | 514/259 |
| 5,247,080 A | 9/1993 | Berger et al. | 540/523 |
| 5,446,069 A | 8/1995 | Shih et al. | 514/681 |
| 5,672,596 A | * 9/1997 | Wyvratt et al. | 514/183 |
| 5,700,827 A | 12/1997 | Schnorrenberg et al. | 514/414 |
| 5,786,353 A | 7/1998 | Albright et al. | 514/211 |
| 6,262,068 B1 | * 7/2001 | Atwal et al. | 514/307 |

FOREIGN PATENT DOCUMENTS

| | | |
|---|---|---|
| WO | WO 91/17162 | 11/1991 |
| WO | WO 93/00095 | 1/1993 |
| WO | WO 94/14776 | 7/1994 |
| WO | WO/95/30687 | 11/1995 |
| WO | WO 97/24336 | 7/1997 |
| WO | WO00/76981 | * 12/2000 |

OTHER PUBLICATIONS

Sadighi et al., "A Highly Active Palladium Catalyst System for the Arylation of Anilines," Tetrahedron Letters 39 (1998), Pergamon Press, pp. 5327–5330.

* cited by examiner

*Primary Examiner*—Bruck Kifle
(74) *Attorney, Agent, or Firm*—Paul E. White, Jr.; Manelli Denison & Selter PLLC

(57) ABSTRACT

This invention relates to substituted 1-benzazepines and derivatives thereof useful as antibacterial agents, to compositions, including pharmaceutical compositions, comprising such compounds, to processes for making these compounds and to methods of using these compounds for killing bacteria or inhibiting bacterial growth.

29 Claims, No Drawings

SUBSTITUTED 1-BENZAZEPINES AND DERIVATIVES THEREOF

This application claims priority to U.S. provisional application No. 60/166,167, filed Nov. 18, 1999 which is hereby incorporated by reference.

FIELD OF THE INVENTION

This invention relates to novel substituted 1-benzazapines and derivatives thereof useful as antibacterials, to pharmaceutical compositions comprising such compounds, to processes for making these compounds and to methods of using these compounds for treating bacterial infections.

BACKGROUND OF THE INVENTION

Benzazepine compounds are useful in a number of pharmaceutical applications. In particular, U.S. Pat. No. 5,786,353 discloses that tricyclic benzazepine is useful as a vasopressin antagonist. U.S. Pat. No. 5,247,080 discloses that substituted benzazepines are useful as intermediates for producing pharmaceutically active compounds, such as intermediates for compounds that have valuable properties in treating psychosis, depression, pain and hypertension. WO 97/24336 discloses a process for the aminocarbonylation of benzazepines and benzodiazepines. These compounds are used as intermediates for preparing pharmaceutically active compounds.

There have been other processes for the preparation of benzazepines. Tetrahydro-1-benzazepines and tetrahydro-1,4-benzodiazepines form the core structure of a variety of pharmaceutically useful compounds. In particular, WO 93/00095 (PCT/US92/05463) and WO 94/14776 (PCT/US93/12436) disclose 7-aminocarbonyl tetrahydro-1-benzazepines and tetrahydro-1,4-benzodiazepines which are reported to be inhibitors of the fibrinogen and vitronectin receptors and useful as inhibitors of platelet aggregation, osteoporosis, angiogenesis and cancer metastasis.

Methods to prepare such compounds typically employ a trisubstituted phenyl derivative as a starting material. The trisubstituted phenyl derivative incorporates two substituents to form the azepine and/or diazepine ring, and a third substituent to introduce the 7-carbonyl substituent. Such starting materials may be difficult and costly to obtain, and may limit the chemistry which may be employed to form the azepine ring. Prior processes generally introduce the aminocarbonyl group into the molecule via a 7-carboxyl group which is coupled to an amino group by conventional methods for forming amide bonds. Methods disclosed in WO 93/00095 and WO 94/14776 are exemplary.

Bacterial infections are a significant and growing medical problem. They occur when the body's immune system cannot prevent the invasion and colonization of the body by disease-causing bacteria. These infections may either be confined to a single organ or tissue, or disseminated throughout the body, and can cause many serious diseases, including pneumonias, endocarditis, osteomyelitis, meningitis, deep-seated soft tissue infections, bacteremia and complicated urinary tract infections.

According to estimates from the United States Centers for Disease Control and Prevention (the "CDC") in 1995, approximately 1.9 million hospital-acquired infections occurred in the United States, accounting for more than $4.5 billion in additional health care costs each year and contributing to more than 88,000 deaths. While overall per capita mortality rates declined in the United States from 1980 to 1992, the per capita mortality rate due to infectious diseases increased 58% over this period, making infectious diseases the third leading cause of death in the United States.

Antibiotics are administered both to prevent bacterial infections and to treat established bacterial diseases. When administered to prevent an infection, antibiotics are given prophylactically, before definitive clinical signs or symptoms of an infection are present. When administered to treat an established infection, antibiotics are often chosen empirically, before diagnostic testing has established the causative bacterium and its susceptibility to specific antibiotics.

Antibiotics work by interfering with a vital bacterial cell function at a specific cellular target, either killing the bacteria or arresting their multiplication, thereby allowing the patient's immune system to clear the bacteria from the body. Currently available antibiotics work on relatively few targets, through mechanisms such as inhibiting protein or cell wall synthesis. These targets tend to be present in all bacteria and are highly similar in structure and function, such that certain antibiotics kill or inhibit growth of a broad range of bacterial species (i.e., broad-spectrum antibiotics).

Major structural classes of antibiotics include beta-lactams, quinolones, macrolides, tetracyclines, aminoglycosides, glycopeptides and trimethoprim combinations. Penicillin, a member of the beta-lactam class (which also includes extended-spectrum penicillins, cephalosporins and carbapenems), was first developed in the 1940s. Nalidixic acid, the earliest member of the quinolone class, was discovered in the 1960s. The creation of broad-spectrum antibiotics began in the 1970s and 1980s, with major advances seen in the 1970s with the development of newer beta-lactams, and in the 1980s with the development of fluoroquinolones. These antibiotics are still being used extensively. No major new class of antibiotics has been discovered and commercialized in the last 20 years. There remains a need to identify new classes of antibiotics to fight bacterial infections and to overcome the increasing resistance by bacteria to currently marketed antibiotics.

However, none of the prior teachings, described above or elsewhere, disclose the novel 1-benzazepine compounds of the present invention or that 1-benzazepines would be useful as antibacterial agents.

It is therefore an object of this invention to prepare 1-benzazepine derivatives that are useful as agents for the treatment of bacterial, viral or fungal infections both in vivo (including but not limited to parenterally and topically) and for inhibiting bacterial, viral or fungal growth, for example on surfaces and in solution.

SUMMARY OF THE INVENTION

The instant invention is directed to novel substituted 1-benzazepine compounds of the Formula (I):

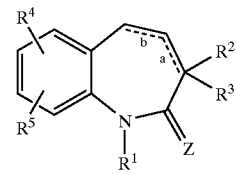

wherein:
$R^1$ is H, with the proviso that $R^4$ and $R^5$ are not both H, substituted or unsubstituted, straight chain, branched or cyclic, alkyl, alkenyl, or alkynyl, substituted or unsubstituted —Ar or —(CH$_2$)$_n$Ar, —(CH$_2$)$_m$C(=O)R, —(CH$_2$)$_n$CN, —(CH$_2$)$_m$C(=Q)OR, —C(=O)N(R)$_2$, —OR, —SO$_2$R, —C(=O)N(H)(NHR), —(CH$_2$)$_n$(OAr), —(CH$_2$)$_n$(OR), —(CH$_2$)$_m$C(=NH)NH$_2$, or —(CH$_2$)$_n$NHRAr;

R$^2$ and R$^3$ are independently H, halogen, —N$_3$, —CN, substituted or unsubstituted, straight chain, branched or cyclic, alkyl, alkenyl, or alkynyl, substituted or unsubstituted —Ar or —(CH$_2$)$_n$Ar, —(CH$_2$)$_m$N(R)$_2$, —(CH$_2$)$_m$NH(Aa), —(CH$_2$)$_m$NC(=O)R, —(CH$_2$)$_m$C(=O)NHOR, —(CH$_2$)$_m$C(=O)OR, —(CH$_2$)C$_m$C(=O)NH(Aa), —(CH$_2$)$_m$C(=O)N(R)$_2$, and —(CH$_2$)$_n$C(=O)NH(Aa), with the proviso that R$^2$ and R$^3$ cannot both be H;

R$^4$ and R$^5$ are independently H, halogen, —NO$_2$, —CN, substituted or unsubstituted, straight chain, branched or cyclic, alkyl, alkenyl, or alkynyl, substituted or unsubstituted —Ar or —(CH$_2$)$_n$Ar, substituted or unsubstituted primary amine or secondary amine, —NHC(=O)R, —NHC(=Q)NHC(=O)OR, —NH(C=Q)NHR, —QR, —OC(=O)N(R$_2$), —C(=O)OR, and —OSi(R)$_3$, with the proviso that R$^4$ and R$^5$ cannot both be H;

Ar is aryl, arylalkyl, heterocycle, heterocyclic group, heterocyclic, heterocyclyl, or heteroaryl;

Aa is —CX(NH$_2$)CO$_2$H, wherein X signifies a group that completes a natural or synthetic amino acid;

R is H, a substituted or unsubstituted straight chain, branched or cyclic lower alkyl, lower alkenyl or lower alkynyl, or a substituted or unsubstituted Ar or (CH$_2$)$_n$Ar;

Q is O or S;

Z is O or S;

a and b are each a single or double bond, and when a is a double bond, only R$^2$ or R$^3$ is present;

m is 0, 1 or 2;

n is 1, 2 or 3;

and pharmaceutically acceptable salts or prodrug forms thereof.

Preferred are compounds of the formula (I) or a pharmaceutically acceptable salt or prodrug form thereof wherein Z is O.

More preferred are compounds of the Formula I, having the formulae II, III, and IV, wherein the substituents are as defined above:

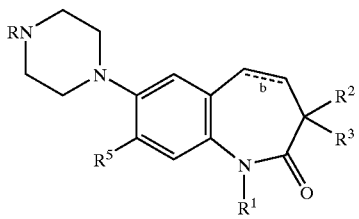

II

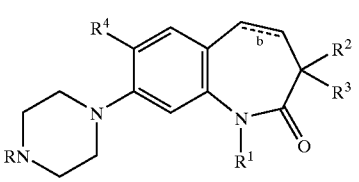

III

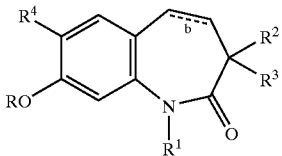

IV

Still more preferred are compounds of the formula (I) or a pharmaceutically acceptable salt or prodrug form thereof wherein R$^2$ and R$^3$ are independently H, halogen substituted or unsubstituted, straight chain, branched or cyclic, alkyl, alkenyl, or alkynyl, substituted or unsubstituted —Ar or —(CH$_2$)$_n$Ar, —(CH$_2$)$_m$C(=O)OR, and —(CH$_2$)$_m$C(=O)NH(Aa) with the proviso that R$^2$ and R$^3$ cannot both be H; one of a or b is a double bond; and m is 0.

Most preferred are compounds of the formulae (II–IV) or a pharmaceutically acceptable salt or prodrug form thereof wherein R$_1$ is H; R$^2$ and R$^3$ are independently H, halogen, substituted or unsubstituted, straight chain, branched or cyclic, alkyl, alkenyl, or alkynyl, substituted or unsubstituted —Ar or —(CH$_2$)$_n$Ar, —(CH$_2$)$_m$C(=O)OR, —(CH$_2$)$_m$C(=O)N(R)$_2$ and —(CH$_2$)$_m$C(=O)NH(Aa) with the proviso that R$^2$ and R$^3$ cannot both be H; R$^4$ and R$_5$ are independently H, halogen, —NO$_2$, —CN, substituted or unsubstituted, straight chain, branched or cyclic, alkyl, alkenyl, or alkynyl, substituted or unsubstituted —Ar or —(CH$_2$)$_n$Ar, substituted or unsubstituted primary amine or secondary amine, and —QR, with the proviso that R$^4$ and R$^5$ cannot both be H; m is 0; Q is O; and Z is O.

Particularly preferred are compounds of the formula (I) or a pharmaceutically acceptable salt or prodrug form thereof wherein R$^1$ is alkyl, alkylfluorophenyl, alkyl nitrile; R$^2$ or R$^3$ is H, halogen, ethyl, propyl, benzyl, fluorobenzyl, —C(=O)OR, —C(=O)OAa and —C(=O)N(R)$_2$ with the proviso that R$^2$ and R$^3$ cannot both be H, R$^4$ and R$^5$ are independently H, halogen, alkoxy, —OR, substituted or unsubstituted piperazinyl with the proviso that R$^4$ and R$^5$ cannot both be H; and a and b are single bonds.

Specifically preferred compounds of the present invention include:

3(R,S)-Carboxyl-1-ethyl-8-methoxy-2,3,4,5-tetrahydro-1H-1-benzazepine-2-one;

1,3-Diethyl-3(R,S)-ethoxycarbonyl-8-methoxy-2,3,4,5-tetrahydro-1H-1-benzazepine-2-one;

3(R,S)-Carboxyl-1,3-diethyl-8-methoxy-2,3,4,5-tetrahydro-1H-1-benzazepine-2-one;

1-Ethyl-8-methoxy-7-[(4-methylpiperazin)-1-yl)]-2,3,4,5-tetrahydro-1H-1-benzazepine-2-one;

3(R,S)-tert-Butoxycarbonyl-8-methoxy-2,3,4,5-tetrahydro-1H-1-benzazepine-2-one;

3(R,S)-tert-Butoxycarbonyl-1-ethyl-8-methoxy-2,3,4,5-tetrahydro-1H-1-benzazepine-2-one;

7-Bromo-3(R,S)-tert-butoxycarbonyl-1-ethyl-8-methoxy-2,3,4,5-tetrahydro-1H-1-benzazepine-2-one;

3(R,S)-tert-Butoxycarbonyl-7-[(4-tert-butoxycarbonylpiperazin)-1-yl]-1-ethyl-8-methoxy-2,3,4,5-tetrahydro-1H-1-benzazepine-2-one;

3(R,S)-Carboxyl-1-ethyl-8-methoxy-7-(piperazin-1-yl)-2,3,4,5-tetrahydro-1H-1-benzazepine-2-one hydrochloride;

3(R,S)-tert-Butoxycarbonyl-1-ethyl-8-methoxy-2,3-dihydro-1H-1-benzazepine-2-one;

7-Bromo-3(R,S)-carboxyl-1-ethyl-8-methoxy-2,3,4,5-tetrahydro-1H-1-benzazepine-2-one;

3(R,S)-tert-Butoxycarbonyl-1-ethyl-8-methoxy-7-(piperazin-1-yl)-2,3,4,5-tetrahydro-1H-1-benzazepine-2-one;

1,4-Di-[(3(R,S)-tert-butoxycarbonyl-1-ethyl-8-methoxy-2-oxo-2,3,4,5-tetrahydro-1H-1-benzazepine)-7-yl]-piperazine;

1,4-Di-[(3(R,S)-carboxyl-1-ethyl-8-methoxy-2-oxo-2,3,4,5-tetrahydro-1H-1-benzazepine)-7-yl]-piperazine;

7-[(4-tert-butoxycarbonylpiperazin)-1-yl]-1-ethyl-8-methoxy-2,3,4,5-tetrahydro-1H-1-benzazepine-2-one;

1-ethyl-8-methoxy-7-(piperazin-1-yl)-2,3,4,5-tetrahydro-1H-1-benzazepine-2-one hydrochloride;

1-tert-Butoxycarbonyl-3(R,S)-tert-butoxycarbonyl-8-methoxy-2,3,4,5-tetrahydro-1H-1-benzazepine-2-one;

3(R,S)-tert-Butoxycarbonyl-1-(3-fluorobenzyl)-8-methoxy-2,3,4,5-tetrahydro-1H-1-benzazepine-2-one;

7-[(4-benzyloxycarbonyl)piperazin-1-yl]-3(R,S)-tert-butoxycarbonyl-1-ethyl-8-methoxy-2,3,4,5-tetrahydro-1H-1-benzazepine-2-one;

3,7-dibromo-1-ethyl-3(R,S)-methoxycarbonyl-8-methoxy-2,3,4,5-tetrahydro-1H-1-benzazepine-2-one;

7-bromo-1-ethyl-3(R,S)-methoxycarbonyl-8-methoxy-2,3,4,5-tetrahydro-1H-1-benzazepine-2-one;

7-bromo-3(R,S)-N-(tert-butyl)aminocarbonyl-1-ethyl-8-methoxy-2,3,4,5-tetrahydro-1H-1-benzazepine-2-one;

7-Bromo-3(R,S)-tert-butoxycarbonyl-1-(3-fluorobenzyl)-8-methoxy-2,3,4,5-tetrahydro-1H-1-benzazepine-2-one;

8-(tert-butyldimethylsilyloxy)-2,3,4,5-tetrahydro-1H-1-benzazepine-2-one;

3(R,S)-tert-butoxycarbonyl-1-cyanomethyl-8-methoxy-7-nitro-2,3,4,5-tetrahydro-1H-1-benzazepine-2-one;

7-[(4-Benzyloxycarbonyl)piperazin-1-yl]-3(R,S)-tert-butoxycarbonyl-1-(3-fluorobenzyl)-8-methoxy-2,3,4,5-tetrahydro-1H-1-benzazepine-2-one; and 7-Bromo-3(R,S)-tert-butoxycarbonyl-8-methoxy-2,3,4,5-tetrahydro-1H-1-benzazepine-2-one or a pharmaceutically acceptable salt or prodrug form thereof.

In the present invention it has been discovered that the compounds above are useful as inhibitors bacterial growth, and for the treatment of bacterial infections.

The present invention also provides methods for the treatment of bacterial, viral or fungal infection by administering to a host infected with bacteria, virus or fungus a pharmaceutically effective amount of a compound of formula (I)

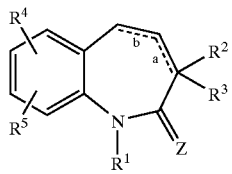

wherein:

$R^1$ is H, substituted or unsubstituted, straight chain, branched or cyclic, alkyl, alkenyl, or alkynyl, substituted or unsubstituted —Ar or —$(CH_2)_n$Ar, —$(CH_2)_m$C(=O)R, —$(CH_2)_m$C(=Q)OR, —C(=O)N(R)_2, —OR, —SO_2R, —C(=O)N(H)(NHR), —CH_2(OR), —$(CH_2)_n$(OAr), —$(CH_2)_m$C(=NH)NH_2, and —$(CH_2)_n$NHAr;

$R^2$ and $R^3$ are independently H, halogen, —$N_3$, —CN, substituted or unsubstituted, straight chain, branched or cyclic, alkyl, alkenyl, or alkynyl, substituted or unsubstituted —Ar or —$(CH_2)_n$Ar, —$(CH_2)_m$N(R)_2, —$(CH_2)_m$NH(Aa), —$(CH_2)_m$NC(=O)R, —$(CH_2)_m$C(=O)OR, —$(CH_2)_m$C(=O)NH(Aa), —$(CH_2)_m$C(=O)N(R)_2, and —$(CH_2)_n$C(=O)NH(Aa);

$R^4$ and $R^5$ are independently H, halogen, —$NO_2$, —CN, substituted or unsubstituted, straight chain, branched or cyclic, alkyl, alkenyl, or alkynyl, substituted or unsubstituted Ar or —$(CH_2)_n$Ar, substituted or unsubstituted primary amine or secondary amine, —NHC(=O)R, —NHC(=Q)NHC(=O)OR, —NHC(=Q)NHR, —QR, —OC(=O)N(R_2), —C(=O)OR, and —OSi(R)_3;

R is H, a substituted or unsubstituted straight chain, branched or cyclic lower alkyl, lower alkenyl or lower alkynyl, or a substituted or unsubstituted Ar or $(CH_2)_n$Ar;

Q is O or S;

Z is O or S;

a and b are each a single or double bond, and when a is a double bond, only $R^2$ or $R^3$ is present;

m is 0, 1 or 2;

n is 1, 2 or 3;

and pharmaceutically acceptable salts or prodrug forms thereof.

Alternatively, the present invention provides compounds and methods for the treatment of central nervous system (CNS) disorders, inflammatory diseases, cardiovascular diseases, cancers including angiogenesis, pain, allergic disorders, autoimmune disorders and immunoregulation.

Another aspect of the invention is directed to processes for making the compounds of the present invention, including the steps of introduction of a carboxyl group into the 1-benzazepine skeleton.

The present invention may be more fully understood by reference to the following detailed description of the invention, non-limiting examples of specific embodiments of the invention.

DESCRIPTION OF THE INVENTION

The compounds of the Formula (I) herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention.

When any variable (for example, $R_1$ through $R^5$, R, Ar, Aa, Q, Z, m, n, etc.) occurs more than one time in any constituent or in formula (I), or any other formula herein, its definition on each occurrence is independent of its definition at every other occurrence. Also, combinations of substituents and/or variables are permissible only if such combinations result in stable compounds.

The term "alkyl" means a branched or unbranched saturated aliphatic hydrocarbon radical, having the number of carbon atoms specified, or if no number is specified, having up to 12 carbon atoms. Examples of alkyl radicals include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like. The terms "lower alkyl" and "$C_1$–$C_6$ alkyl" are synonymous and used interchangeably. A preferred "$C_1$–$C_6$ alkyl" group is methyl or ethyl.

The term "alkenyl" means a branched or unbranched hydrocarbon radical having the number of carbon atoms designated containing one or more carbon-carbon double bonds, each double bond being independently cis, trans, or a nongeometric isomer.

The term "alkynyl" means a branched or unbranched hydrocarbon radical having the number of carbon atoms designated containing one or more carbon-carbon triple bonds.

The term "substituted alkyl, alkenyl, alkynyl" denotes the above alkyl, alkenyl or alkynyl groups that are substituted by one, two or three; halogen (F, Cl, Br, I), nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, and methylsulfonylamino. The substituted alkyl, alkenyl, and alkynyl groups may be substituted once, twice or three times with the same or with different substituents.

Examples of the above substituted alkyl groups include but are not limited to: cyanomethyl, nitromethyl, hydroxymethyl, trityloxymethyl, propionyloxymethyl, aminomethyl, carboxymethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(isopropyl), 2-carbamoyloxyethyl and the like. A preferred group of examples within the above "substituted alkyl" group includes the substituted methyl group and substituted ethyl group. Examples of the substituted methyl group include groups such as hydroxymethyl, protected hydroxymethyl (e.g., tetrahydro-pyranyloxymethyl), acetoxymethyl, carbamoyloxymethyl, trifluoromethyl, chloromethyl, bromomethyl and iodomethyl.

The terms "alkyloxy" or "alkoxy" are used interchangeably herein and denote groups such as methoxy, ethoxy, n-propoxy, isopropoxy, n-butoxy, t-butoxy and like groups.

The terms "acyloxy" or "alkanoyloxy" are used interchangeably and denote herein groups such as formyloxy, acetoxy, propionyloxy, butyryloxy, pentanoyloxy, hexanoyloxy, heptanoyloxy and the like.

The terms "alkylcarbonyl", "alkanoyl" and "acyl" are used interchangeably herein encompass groups such as formyl, acetyl, propionyl, butyryl, pentanoyl, hexanoyl, heptanoyl, benzoyl and the like.

The term "cycloalkyl" as used herein refers to a mono-, bi- or tricyclic aliphatic ring having 3 to 14 carbon atoms and preferably 3 to 7 carbon atoms.

The terms "alkylthio" and "substituted alkylthio" denote alkyl and substituted alkyl groups, respectively, attached to a sulfur which is in turn the point of attachment of the alkythio or substituted alkylthio group to the group or substituent designated.

The term "Ar" as used herein and in the claims denotes any partially saturated aromatic, or aromatic, aryl, arylalkyl, heterocycle, heterocyclic group, heterocyclic, heterocyclyl, and heteroaryl generally known to those skilled in organic chemistry and as further described herein below.

The term "Substituted Ar" denotes any substituted, partially saturated aromatic, or aromatic, aryl, substituted arylalkyl, and substituted heteroaryl which are generally known to those skilled in organic chemistry and as further described herein below, that include but are not limited to those groups wherein one or more hydrogens are substituted by one, two or three: halogen (F, Cl, Br, I), nitro, cyano, hydroxy, protected hydroxy, alkoxy, haloalkoxy, cyclic, branched or unbranched lower alkyl, cyclic, branched or unbranched lower alkenyl, cyclic, branched or unbranched lower alkynyl, substituted with amino, protected amino, cyano, nitro, aminomethyl, $C_1$–$C_6$ acyloxy, carboxy, protected carboxy, carboxymethyl, hydroxymethyl, carbamoyl, carbamoyloxy, trifluoromethyl, N-(methylsulfonylamino), methylsulfonylamino or other groups specified.

The term "aryl" denotes any mono-, bi- or tricyclic partially saturated aromatic ring or aromatic ring having 5–21 carbon atoms, where at least one ring is a 5-, 6- or 7-membered hydrocarbon ring, and containing from zero to four heteroatoms selected from nitrogen, oxygen and sulfur. Preferred hydrocarbon aryl groups include phenyl, napthyl, biphenyl, phenanthrenyl, naphthacenyl and the like (see *Lang's Handbook of Chemistry* (Dean, J. A., ed) $14^{th}$ Ed., [1992]).

Examples of the term "substituted phenyl" include but are not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorphenyl, 2-fluorophenyl and the like; a group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 2,6-dimethoxyphenyl, 4-methoxyphenyl, 3-ethoxyphenyl, 4-(iso-propoxy)phenyl, 4-(t-butoxy)phenyl, 3-ethoxyphenyl-4-methoxyphenyl and the like; 3- or 4-trifluoromethylphenyl; a mono- or dicarboxyphenyl or (protected carboxy)phenyl group such as 4-carboxyphenyl; a mono- or di(hydroxymethyl)phenyl or (protected hydroxymethyl)phenyl such as 3-(protected hydroxymethly)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino)phenyl.

Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The term "arylalkyl" means one, two or three aryl groups having 3 to 14 carbon atoms, appended to an alkyl radical having 1 to 12 carbon atoms including but not limited to: benzyl, napthylmethyl, phenethyl, benzyhydryl (diphenylmethyl), trityl piperazinylmethyl, pyrimidinylethyl, pyridazinylpropyl, indolylbutyl, purinylmethyl and the like.

The term "substituted arylalkyl" denotes an alkyl group substituted at any carbon with a $C_6$–$C_{12}$ aryl group bonded to the alkyl group through any aryl ring position and substituted on the $C_1$–$C_6$ alkyl portion with one, two or three groups chosen from halogen (F, Cl, Br, I), straight chain, branched or cyclic $C_1$–$C_6$ alkyl, straight chain, branched or cyclic $C_1$–$C_6$ alkenyl, straight chain, branched or cyclic $C_1$–$C_6$ alkynyl, hydroxy, protected hydroxy, amino, protected amino, $C_1$–$C_6$ acyloxy, nitro, carboxy, protected carboxy, carbamoyl, carbamoyloxy, cyano, $C_1$–$C_6$ alkylthio, N-(methylsulfonylamino) or $C_1$–$C_6$ alkoxy. Optionally, the aryl group may be substituted with one, two or three groups chosen from halogen, straight chain, branched or cyclic $C_1$–$C_6$ alkyl, straight chain, branched or cyclic $C_1$–$C_6$ alkenyl, straight chain, branched or cyclic $C_1$–$C_6$ alkynyl, hydroxy, protected hydroxy, nitro, $C_1$–$C_6$ alkyl, $C_1$–$C_4$ alkoxy, carboxy, protected carboxy, carboxymethyl, protected carboxymethyl, hydroxymethyl, protected hydroxymethyl, aminomethyl, protected aminomethyl or an N-(methylsulfonylamino) group. As before, when either the $C_1$–$C_6$ alkyl portion or the aryl portion or both are disubstituted, the substituents can be the same or different.

Examples of the term "substituted arylalkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), and the like.

Unless otherwise specified, the terms "heterocycle", "heterocyclic group", "heterocyclic" or "heterocyclyl" are used interchangeably herein and includes any mono-, bi- or tricyclic saturated, unsaturated or aromatic ring where at least one ring is a 5-, 6- or 7-membered hydrocarbon ring containing from one to four heteroatoms selected from nitrogen, oxygen and sulfur, preferably at least one heteroatom is nitrogen (*Lang's Handbook of Chemistry*, vide supra).

Preferably, the heterocycle is a 5- or 6-member saturated, unsaturated or aromatic hydrocarbon ring containing 1, 2, or 3 heteroatoms selected from O, N and S. Typically, the 5-membered ring has 0 to 2 double bonds and the 6- or 7-membered ring has 0 to 3 double bonds and the nitrogen or sulfur heteroatoms may optionally be oxidized, and any nitrogen heteroatom may optionally be quarternized. Included in the definition are any bicyclic groups where any of the above heterocyclic rings are fused to a benzene ring. Heterocyclics in which nitrogen is the heteroatom are preferred.

The following ring systems are examples of the heterocyclic (whether substituted or unsubstituted) radicals denoted by the term "heterocyclic": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, dihydropyrimidyl, tetrahydropyrimidyl, tetrazolo-[1,5b]-pyridazinyl and purinyl, as well as benzo-fused derivatives for example benzoxazolyl, benzthiazolyl, benzimidazolyl and indolyl.

Heterocyclic 5-membered ring systems containing a sulfur or oxygen atom and one to three nitrogen atoms are also suitable for use in the instant invention. Examples of such preferred groups included thiazolyl in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl and tetrazolyl, preferably 1H-tetrazol-5-yl. A preferred group of examples of benzo-fused derivatives are benzoxazol-2-yl, benzthiazol-2-yl and benzimidazol-2-yl.

Further suitable specific examples of the above heterocylic ring systems are 6-membered ring systems containing one to three nitrogen atoms. Such examples include pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl and pyrazinyl. The pyridine N-oxides and pyridazine N-oxides and the pyridyl, pyrimid-2-yl, pyrimid-4-yl, pyridazinyl and the 1,3,4-triazin-2-yl radicals are a preferred group. Optionally, preferred 6-membered ring heterocycles are: piperazinyl, piperazin-2-yl, piperidyl, piperid-2-yl, piperid-3-yl, piperid-4-yl, morpholino, morpholin-2-yl and morpholin-3-yl.

The substituents for the optionally substituted heterocyclic ring systems and further examples of the 6- and 7-membered ring systems discussed above can be found in W. Durckheimer, et. al, U.S. Pat. No. 4,278,793.

An optionally preferred group of "heterocyclics" include: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-oxadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(N-oxide)-pyridazin-3-yl, 6-hydroxypyridazin-3-yl, 1-methylpyridin-2-yl, 1-methylpyridin-4-yl, 2-hydroxypyrimidin-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heterocyclics" includes: 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1-H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl,tetrazolo[1,5-b]pyridazin-6-yl and 8-aminotetrazolo[1,5-b]pyridazin-6-yl.

The terms "heteroaryl group" or "heteroaryl" are used interchangeably herein and includes any mono-, bi- or tricyclic aromatic rings having the number of ring atoms designated where at least one ring is a 5-, 6- or 7-membered hydrocarbon ring containing from one to four heteroatoms selected from nitrogen, oxygen and sulfur, preferably at least one heteroatom is nitrogen. The aryl portion of the term "heteroaryl" refers to aromaticity, a term known to those skilled in the art and defined in greater detail in "*Advanced Organic Chemistry*", J. March, 4$^{th}$ Ed., John Wiley & Sons, New York, N.Y. (1992).

The term "Aa" as used herein and in the claims refers to "amino carboxylic acid" as that term is generally understood by those skilled in the art and denotes any group having —CX(NH$_2$CO$_2$H), wherein X signifies a group that completes a natural or synthetic amino acid. Typical natural aminoacids include but are not limited to alanine, arginine, asparagine, aspartic acid, cysteine, glutamine, glutamic acid, glycine, histidine, isoleucine, leucine, lysine, methionine, phenyl-alanine, proline, serine, threonine, tryptophan, tyrosine, and valine. Any other amino acid, natural or synthetic, are contemplated within the scope of this invention.

The term "primary amine" as used herein and in the claims is generally understood by those skilled in the art and denotes any group which is attached to an amine (—NH$_2$) moiety, and includes but is not limited to alkyl-amines, alkenyl-amines, alkynyl-amines, aryl-amines and herteroaryl-amines, as such terms are described herein above.

Examples of primary amines include, but are not limited to any of those listed above, as well as for example, guanidine, methylguanidine, 1,10-diaminodecane, 1,4-diaminobutane, 5-amino-indazole, 7-amino-4-(trifluoromethyl)-coumarin, 4-bromo-3-(trifluoromethyl) aniline, 3-chloro-4-fluoroaniline, 2-chloro-5-(trifluoromethyl)aniline, 3,5-difluorobenzylamine, 2-(difluoromethoxy)aniline, 3-fluoro-p-anisidine, 2-fluoroethylamine, 3-fluoro-4-methylaniline, 4-fluorophenylethylamine, 3-fluoro-d-phenylalanine, 3-fluoro-1-phenylalanine, d,1,-3-fluorophenylalanine, 4-fluoro-3-(trifluoromethyl)benzylamine, 6-fluoro-tryptamine, 5-fluoro-1-tryptophan, 5-fluoro-d,1,-tryptophan, 4-(trifluoromethyl)aniline, 4-(trifluoromethyl)benzylamine, 4-(trifluoromethylthio)aniline, and 2-(4-morpholino) ethylamine.

The term "secondary amine" as used herein and in the claims is generally understood by those skilled in the art and denotes any two groups which are attached symmetrically or unsymmetrically to an amino (—NH—) moiety.

Examples of secondary amines include, but are not limited to any of those listed above, as well as for example, piperazine, pyrrolidine, 3-(tert-butoxycarbonylamino)-pyrrolidine, 1-benzylpiperazine, benzyl-1-piperazine carboxylate, 4-benzylpiperidine, 1-(2-chlorophenyl) piperazine, 2,6 dimethylmorpholine, ethyl isonipecotate, ethyl-1-piperazinecarboxylate, 1-(4-fluorophenyl) piperazine, heptamethyleneimine, 1-(2-methoxyphenyl) piperazine, 1-methylhomopiperazine, 1-methylpiperazine, morpholine, 1-(4-nitrophenyl)piperazine, 1-phenylpiperazine, 1-phenylpiperazine, 4'-piperazinoacetophenone, piperidine, 4-piperidinopiperadine, 1-(2-pyridyl)piperazine, 1-(2-pyrimidyl)piperazine, 4-(1-pyrrolidinyl)piperidine, 1,2,3,4-tetrahydroisoquinoline, thiomorpholine, 1-(o-tolyl) piperazine, 1-(α,α, α,trifluoro-m-tolyl)piperazine, 1-(2,3-xylyl)piperazine, tert-butyl-1-piperazinecarboxylate, 1-(2,5-dimethylphenyl)piperazine, 4,4'-bipiperidine, cis-2,6-dimethylpiperazine, and 3,5-dimethylpiperazine.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 19th ed., Mack Publishing Company, Easton, Pa., 1995, p. 1418, the disclosure of which is hereby incorporated by reference.

Pharmaceutically acceptable acid addition salts are those salts which retain the biological effectiveness and properties of the free bases and which are not biologcially or otherwise undesirable, formed with inorganic acids such as hydrochloric acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

Pharmaceutically acceptable base addition salts are those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethylamine, dicyclohexylamine, choline and caffeine.

"Prodrugs" are considered to be any covalently bonded carriers which release the active parent drug in vivo when such prodrug is administered to a subject. Prodrugs of the compounds of the parent compound are prepared by modifying functional groups present in the compounds in such a way that the modifications are cleaved, either in routine manipulation or in vivo, to the parent compounds. Prodrugs include, but are not limited to, compounds wherein hydroxy, amine, or sulfhydryl groups are bonded to any group that, when administered to a subject, cleaves to form a free hydroxyl, amino, or sulfhydryl group, respectively. Examples of prodrugs include, but are not limited to, acetate, formate and benzoate derivatives of alcohol and acetyl and benzoyl derivatives of amine functional groups in the compounds of the invention and the like.

By "stable compound" or "stable structure" is meant herein a compound that is sufficiently robust to survive isolation to a useful degree of purity from a reaction mixture, and formulation into an efficacious therapeutic agent.

Synthesis

There are many ways well known by those skilled in the art of organic chemistry to prepare the compounds of the present invention. Some of these are described by the General Schemes A to D and specific examples presented below. Each of the references cited below and elsewhere within are hereby incorporated herein by reference in their entireties.

General transformations are well reviewed in "Comprehensive Organic Transformation" by Richard Larock and the following series: "Organic Syntheses", Collective Volumes 1 to 9, "Compendium of Organic Synthetic Methods" and "Reagents for Organic Synthesis" by Fieser & Fieser. Protecting groups may be used when appropriate throughout general and specific schemes of this invention. The choice and use of protecting groups is well known in the art and is not limited to the specific examples bellow. A general reference for protecting group preparation and deprotection is "Protecting Groups in Organic Synthesis" by Theodora Green.

The term "carboxy-protecting group" as used herein refers to one of the ester derivatives of the carboxylic acid group commonly employed to block or protect the carboxylic acid group while reactions are carried out on other functional groups of the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4', 4"trimethoxytrityl, 2-phenylprop-2-yl, trimethylsilyl, t-butyldimethylsilyl, 2,2,2-trichloroethyl, β-(trimethylsilyl) ethyl, β-(di(n-butyl)methylsilyl)ethyl, p-toluenesulfonylethyl, 4-nitrobenzylsulfonylethyl, allyl, cinnamyl, 1-(trimethylsilyl)prop-1-en-3-yl and like moieties. The species of carboxy-protecting group employed is not critical so long as the derivatized carboxylic acid is stable to the condition of subsequent reaction(s) on other positions of the 1-benzazepine molecule and can be removed at the appropriate point without disrupting the remainder of the molecule. In particular, it is important not to subject the carboxy-protected 1-benzazepine molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl, tert-butyl and p-nitrobenzyl groups. Similar carboxy-protecting groups used in the cephalosporin, penicillin and peptide arts can also be used to protect a carboxy group substituents of the 1-benzazepine.

As used herein, the term "amino-protecting group" refers to any group typically used in the peptide art for protecting the peptide nitrogens from undesirable side reactions. Such groups include 3,4-dimethoxybenzyl, benzyl, p-nitrobenzyl, di-(p-methoxyphenyl)methyl, triphenymethyl, (p-methoxyphenyl)diphenylmethyl, N-5-dibenzosuberyl, trimethylsilyl, t-butyl dimethylsilyl and the like. Further descriptions of these protecting groups can be found in *"Protective Groups in Organic Synthesis"* by Theodora W. Greene, 1999, John Wiley and Sons, New York, N.Y.

General Schemes

In general the starting materials were obtained from commercial sources unless otherwise indicated. The compounds of the present invention may be synthesized from the key intermediate 3 shown in General Scheme A. Benzo-fused lactams 3 are conveniently prepared from appropriately substituted α-tetralones which are, in some cases, commercially available. In addition, substituted a-tetralones are well known in the art of organic synthesis and numerous methods for their preparation are published. Conversion of substituted α-tetralones 1 to benzo-fused lactams 3 can be achieved by a number of methods proceeding via the intermediate, corresponding oxime 2, that may be isolated or used as is. Suitable methods for transformation 1 to 3 involve the use of the Beckmann Rearrangement or Schmidt reaction. The key intermediate 3 is then deprotonated with an inert base such as LDA or Li-hexamethyl disilazide and the like. Typically such reactions are carried out in, for instance, but not limited to THF, dioxane, ether at temperatures −78° C. to 25° C. Numerous electrophilic reagents can capture an anion, formed on α-position relative to amide functionality. In some cases, the intermediate 4 may be again reacted with an inert base in an inert solvent, followed by an attack of an electrophile to give disubstituted products on 3-position of the 1-benzazepine-2-one ring. Subsequently, an alkyl group may be introduced on the hetero-atom as shown in General Scheme A. Typically bases may include, but are not limited to $Cs_2CO_3$, $K_2CO_3$, NaH, KH while alkylating reagents would include, but are not limited to ethyl bromide, ethyl iodide, diethyl sulfate, 2-bromoethanol and the like. Solvents would include, but are not limited to acetonitrile, acetone, DMA, DMF and the like. Alkylations of this kind are usually run at 25° C. to 100° C. Thus obtained intermediate 5 may represent a final NCE or may be further elaborated.

GENERAL SCHEME A

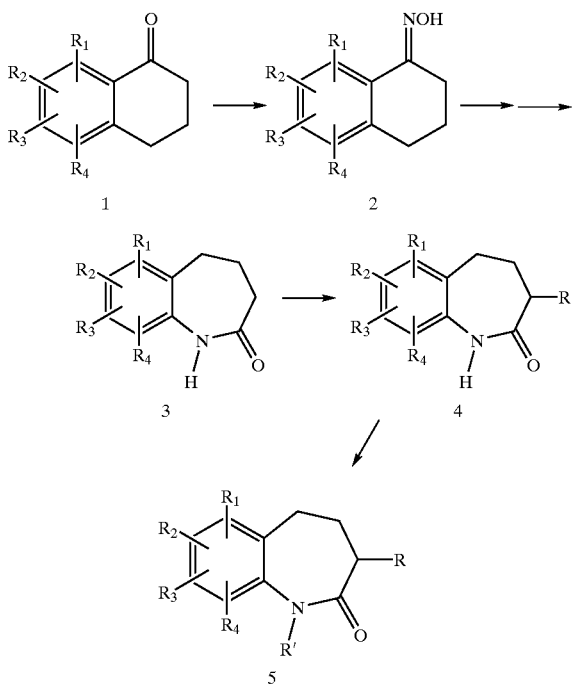

In General Scheme B, the synthetic sequence for an appendage of an amino functionality on aromatic ring of benzo-fused lactams is depicted. Intermediate 5 can be halogenated on the aromatic ring using the methods well known in the art. Preferred halogens are bromo, iodo and chloro because of the feasibility of the subsequent palladium catalyzed coupling reaction. Typically bromination reagents would include, but are not limited to N-bromosuccinimide, N-bromosuccinimide+co-reagent, N-bromoacetamide, bromine, bromine+co-reagent, pyridinium bromide perbromide and the like. Commonly, chloroform, carbon tetrachloride, THF, dioxane, DMF, DMA, DMSO and the like are used as solvents at 25° C. to 100° C. These reactions require 2 to 12 hours. Intermediate 6 is converted to intermediate 7 by using an analogous methodology to that of palladium catalyzed amination of aryl bromides. Detailed reaction conditions for the latter coupling reactions are summarized in a discussion of the Specific Scheme 3 (vide infra). The method employed is taken from Sadighi J. P., et al. (1998) Tetrahedron Letters 39:5327. Displacement of a halogeno leaving group includes, but is not limited to, nitrogen heterocycles. Other primary and secondary alkyl/aryl amines would also displace Br, Cl and I leaving groups. The 7-bromo of the intermediate 6 is displaced preferentially using a nucleophilic amine such as piperazine, methyl piperazine, tert-butyl 1-piperazinecarboxylate and benzyl 1-perazinecarboxylate. Co-bases such as $K_2CO_3$, $Cs_2CO_3$, $NaOBu^t$, $KOBu^t$, $K_3PO_4$ and the like are usually used to capture hydrogen halides that are generated in the relevant reactions. This type of reaction is performed in toluene, xylenes, acetonitrile, DMA, THF, DMF at 25° C. to 120° C. and requires 2 to 48 hours. In Schemes B and C, $R_4Y$ represents a compound wherein $R_4$ is defined according to the invention and Y is a leaving group that allows $R_4$ to be inserted into the ring. Y includes but is not limited to —$SnBu_3$ (tributyl tin), $Sn(CH_3)_3$ and —$B(OH)_2$.

In addition to amination of the intermediate 6, carbocyles, aryls and heteroaryls may also be introduced at X on the benzo-fused lactams ring when X is Br, I, Cl or triflate using palladium or cupric catalyzed couplings of tin or boronate carbocycles, aryls and heteroaryls. The relevant methodologies are well known in the art and are described by literature methods such as those published by Chan D. M. T., et al (vide infra); Kamikawa K., et al J. Org. Chem. 1998, 63, 8407–8410 and Stille, et al., Angew. Chem. Int. Ed.Eng.1986, 25,508. Recently reported advances in the field of Suzuki-type reactions include the development of improved conditions for the coupling of arylboronic acids with aryl chlorides catalyzed by either palladium or nickel complexes as reported in the following publications: Tetrahedron Lett. 1997, 38, 5575; Tetrahedron Lett. 1997, 38, 3513; J. Org. Chem., 1997, 62, 8024.

Hydroxy, alkoxy and aryloxy groups may be introduced in 1-benzazepine 2-one system as shown in General Scheme C. It should be noted that groups $R_1$, $R_2$, $R_3$ of the starting compound 8 could be chosen from an array of groups or precursors thereof indicated in the Structural Formula I. When one of the substituents on the aromatic ring of the benzo- fused seven membered lactam is a methoxy group it can be deprotected using $BBr_3$, $BI_3$, $AlI_3$, $AlCl_3$, $AlCl_3$+ NaSEt, HBr/AcOH or any other appropriate reagent known in the deprotection art. Solvents such as DCM, chloroform, toluene are generally employed in the latter deprotection reactions which are run at ambient temperature to 70° C. and require 2 hours to 48 hours. The resulting hydroxyl group should be protected again in order to further embellish the intermediate 9 according to the synthetic steps that follow those of the General Scheme A. The dimethyl tert-butyl silyl protecting group of the intermediate 12 may be removed by tetrabutylammonium fluoride or acid treatment.

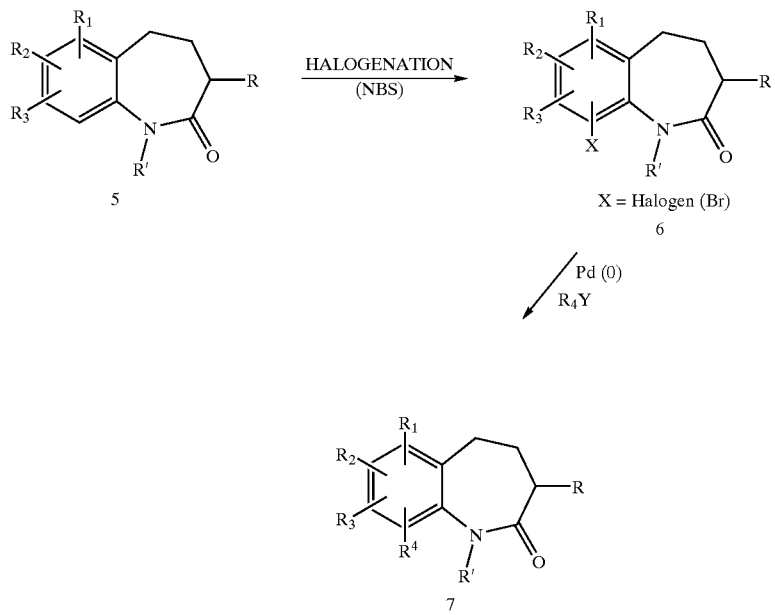

GENERAL SCHEME B

GENERAL SCHEME C

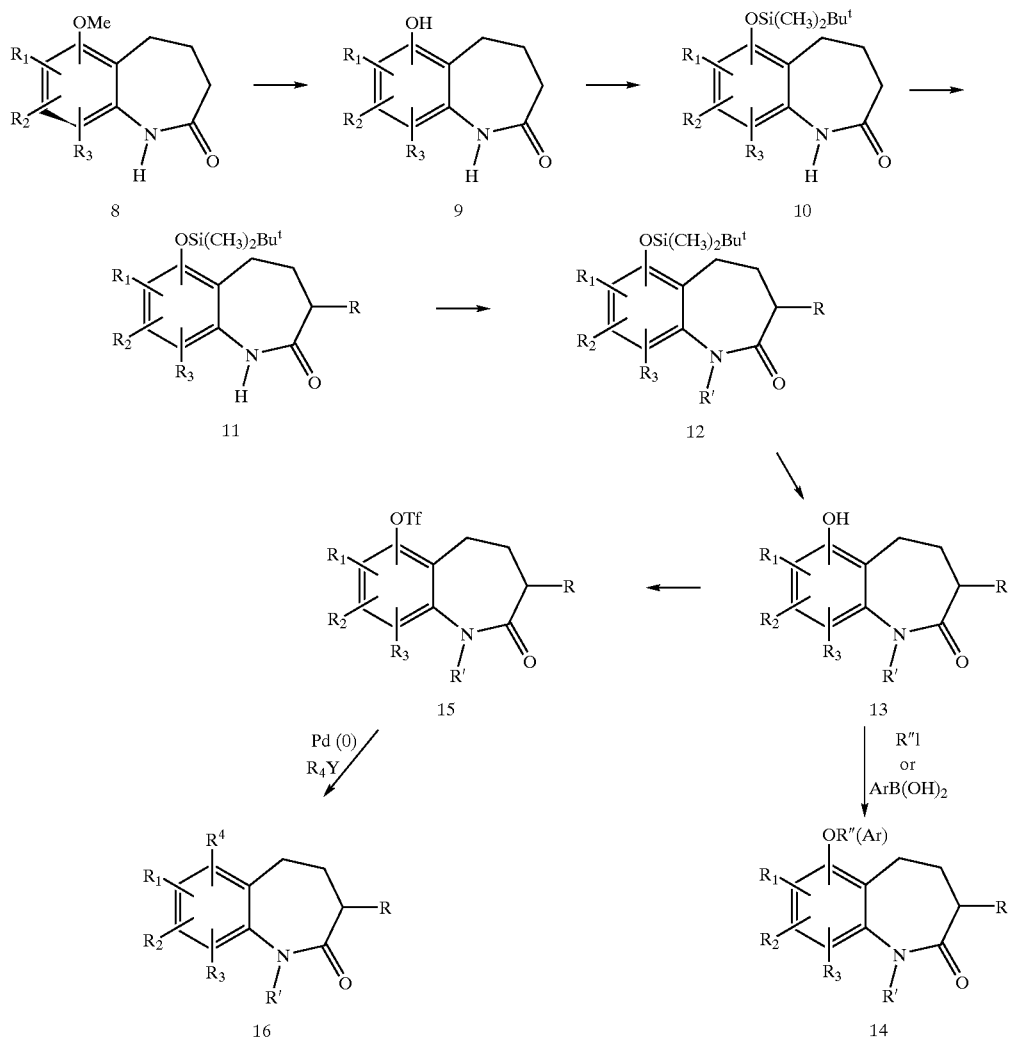

An alkylation of 13 can be carried out with inert bases such as $K_2CO_3$, $Cs_2CO_3$, $NaHCO_3$ and the like. Solvents are typically, but are not limited to dioxane, DMF, DMA, and DMSO, acetone, acetonitrile and the like. Temperatures are 25° C. to 125° C. Alkylating reagents in the latter cases are limited to alkyl and substituted benzyl iodides and bromides.

In a transformation of 13 to 14 where R″ equals aryl the use of the boronic acids in forming a heteroatom-carbon bond has been employed. Indeed, intermediate 13 appears to be an appropriate substrate for O-arylations with phenylboronic acids and cupric acetate as described by Evans, D. A., et al; in Tetrahedron Lett., 1998, 39, 2937–2940 and Chan D. M. T., et al, in Tetrahedron Lett. 1998, 39, 2933–2936. An alternative methodology for O-arylations is an analogous method to that of the tertiary amine promoted reaction of N—H bonds with triarylbismuth and cupric acetate. It is known in the art of organic synthesis that phenylboronic acids are also efficient arylating agents and the relevant reaction represents a relatively new, robust, and convenient methodology to arylate O—H and N—H bonds containing compounds. Thus, using essentially the same reaction conditions as in the triarylbismuth arylation as originally reported by Burton (Barton, D. H. R., et al; Tetrahedron Lett. 1987, 28, 887–890) one can in many cases replace the bismuth reagent with the corresponding arylboronic acids. We believe that the latter reaction is broadly applicable to a large variety of the substituted 1-benzazepines-2-one substrates and is also very tolerant to many sensitive functional groups. As in the bismuth arylation, the reaction can be performed under very mild reaction conditions, i.e. room temperature and with an amine base. It should be noted that the yield of the reaction can be quite dependent on the nature of the substrate and the substitution on the boronic acid. The choice of the tertiary amine base, i.e., triethylamine versus pyridine also plays a critical role in determining the yield of the reaction. Arylboronic acids in place of triarylbismuth represent an attractive alterantive in O-arylations since a large number of organo boronic acids are either commercially available or their syntheses are well described in the literature. Some arylboronic acids can be obtained from Aldrich Chem Corp. or Lancaster Synthesis Inc., and can be used without further purification.

The phenol type derivative 13 of substituted 1-benzazepine-2-one can be transformed into the corresponding triflate intermediate by any method known in the protecting art. Subsequently, the intermediate 15 can be subjected to a coupling reaction with a variety of the amines using Pd(0) catalyst mediated reactions. When the leaving group is a triflate, organotin reagents and organoboronates may be used with palladium catalysts to render a carbon nucleophile. In this way all sorts of alkyl, aryl and heteroaryl groups may be introduced in the 1-benzazepine-2-one ring as it was discussed before and indicated in the General Scheme B.

In General Scheme D, synthetic methodologies to prepare 1-benzazepines-2-ones bearing an additional oxo group on 5-position and a double bond at different positions of seven membered lactam ring are shown.

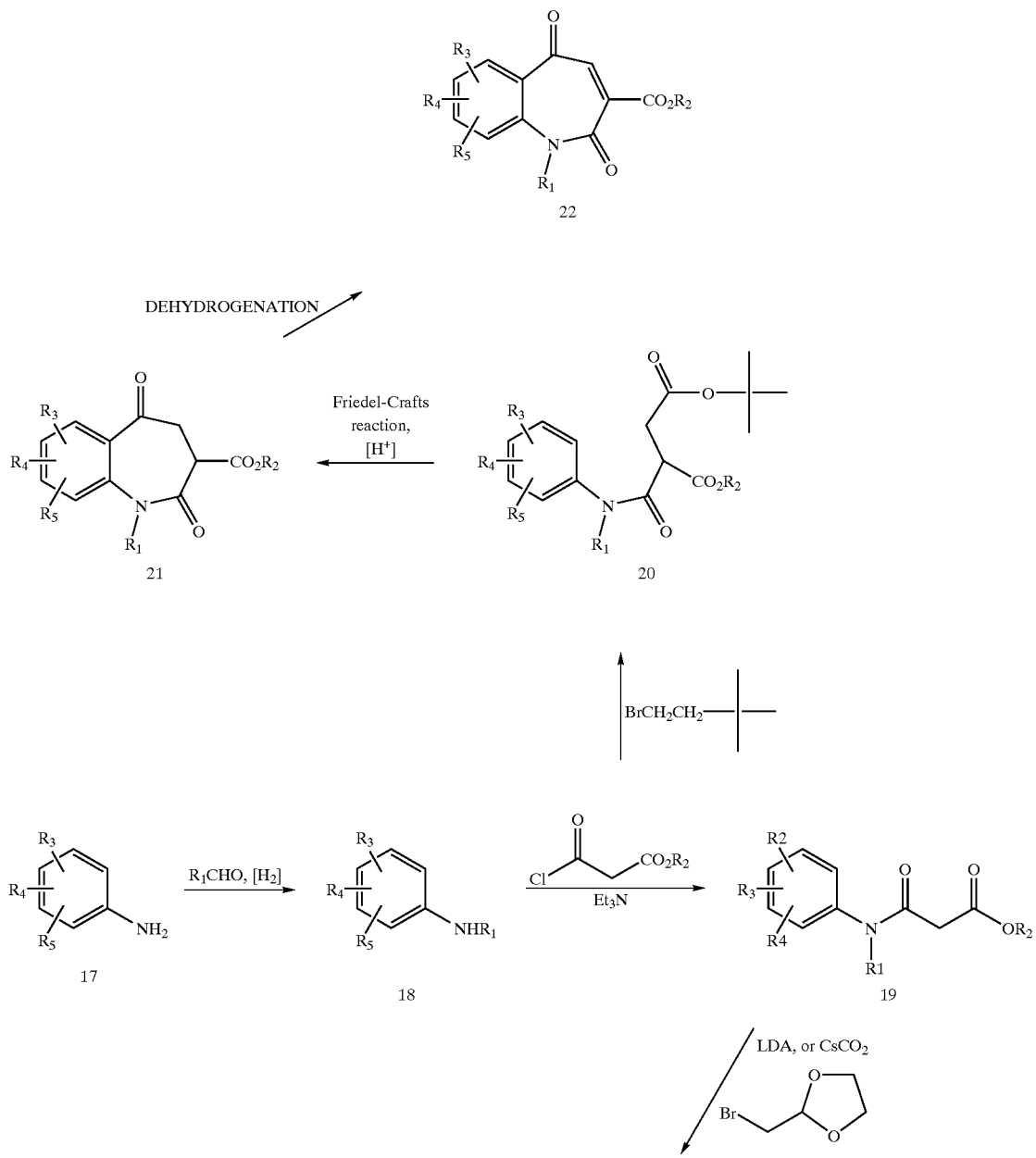

-continued

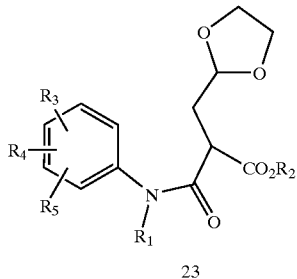

23

[H+]/

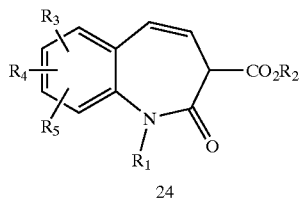

24

Substituted anilines, exemplified by 17, serve as a starting material, which can be alkylated by using reductive condensation with a variety of aldehydes (alkyl, aryl and heteroaryl). It should be noted that the substituents $R_3$, $R_4$, $R_5$ of the starting aniline 17 can be chosen from an array of groups that are indicated on the aromatic ring in the Structural Formula I. Reductive aminations are well known in the art and are typically performed in alcohols, water/alcohol mixtures or in water/DMF mixtures at temperatures 25° C. to 80° C. Thus obtained N-alkylated anilines can be further acylated using any 3-chloro 3-oxopropionate (alkyl/benzyl malonyl chloride) as a reagent of choice to synthesize the intermediate 19 as shown in General Scheme D. The ester group of the intermediate 19 can be later in the synthesis transformed into carboxyl, amino carbonyl or hydroxymethyl group. The 19-type intermediates are very well known in the chemistry of quinolones. Elongation of a carbon chain on the hetero-atom with tert-butylbromoacetate, for instance, provides an appropriate substrate for a subsequent Friedel Crafts reaction. Typically these reactions are run in the presence of inert bases such as LDA, Li-hexamethyl disilazide and the like. Solvents would typically include THF, ether, 1,4-dioxane and DMF at temperatures −78° C. and 25° C.

A cyclization of 20 can be achieved by a number of methods well known in the literature as Friedel-Crafts reaction. A cyclization of 20 to 21 can be effected, for instance, in one pot reaction via the mixed anhydride formed with triflic acid. Introduction of a double bond is examplified but not limited to a conversion of 21 to 22.

Dehydrogenation of the intermediate 21 can be carried out using diphenyl diselenide+LDA, phenylselenyl chloride, DDQ, benzeneselenic anhydride, formed in situ, selenium dioxide in water or any appropriate reagent known in the dehydrogenation art. Typically solvents would include dioxane, THF, benzene, chlorobenzene, acetic acid, ethanol at temperatures 25° C. to 120° C. These latter reactions usually require 2 hrs to 48 hours.

When a prolongation of the chain on the hetero-atom of the intermediate 19 is effected by using bromoacetaldehyde ethylene acetal, for instance, in the presence of inert bases such as LDA or $Cs_2CO_3$ the intermediate 23 is obtained.

Subsequent cyclizatin of 23, followed by a dehydration in strong acidic reaction conditions affords the desired compound 24. Typically strong acids would include p-toluene sulfonic acid or PPA at elevated temperatures. 24 can be considered a NCE or an intermediate that can be further embellished.

Specific compounds depicted by a general formula I of the present invention can be prepared from 8-methoxy-2,3,4,5-tetrahydro-1H-1-benzazepine-2-one (3A) as a common intermediate. The preparation of some key intermediates and final NCEs are described in the following reaction schemes:

Schemes 1, 2, 3, 4, 5, and 6. The syntheses of some intermediates in this instant invention are described in a narrative way.

8-methoxy-2,3,4,5-tetrahydro-1H-1-benzazepine-2-one (3A) is conveniently prepared from 7-methoxy-1-tetralone (1A), using known procedures described by Eaton, et al, J. Org. Chem. (1973) 38, 4071. 7-Methoxy-1-tetralone, which is commercially available, was transformed to 8-methoxy-2,3,4,5-tetrahydro-1H-1-benzazepine-2-one (3A) via the corresponding oxime (2A) followed by the Beckmann rearrangement as illustrated in Scheme 1. The Beckmann rearrangement can be achieved by a number of methods well known in the literature, including treatment of 7-methoxy-1-tetralone oxime (2A) with methanesulfonic acid and anhydrous phosphorous pentoxide at elevated temperatures.

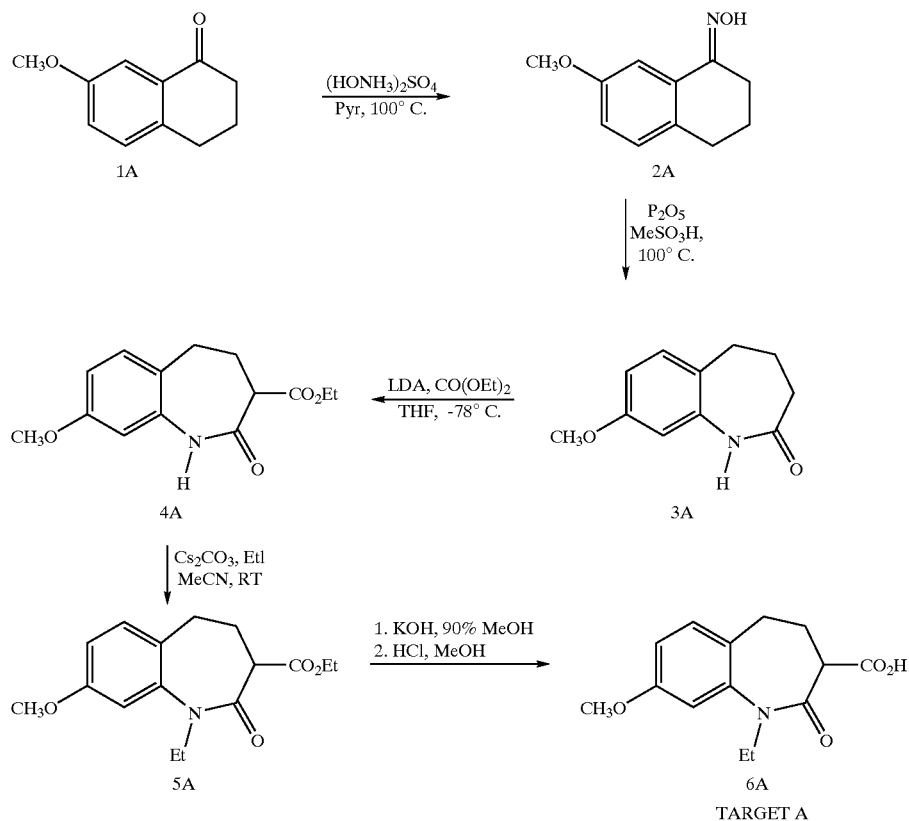

8-Hydroxy-2,3,4,5-tetrahydro-1H-1-benzazepine-2-one was designed to investigate utility of boron tribromide as a deprotective agent for the 1-benzazepine-2-one substrate bearing methoxy group. Deprotection of 8-methoxy-2,3,4,5-tetrahydro-1H-1-benzazepine-2-one using $BBr_3$ in DCM was successful. Other substituted 1-benzazepine-2-ones bearing the methoxy functionality are deemed to be subjected to the above-mentioned deprotection. Therein also lies a problem-applicability of this deprotection reaction conditions to 8-methoxy-1-benzazepine-2-ones bearing tert-butoxycarbonyl group.

Conversion of 8-methoxy-2,3,4,5-tetrahydro-1H-1-benzazepine-2-one (3A) to the 3-ethoxycarbonyl intermediate (4A) can be achieved by a number of methods familiar to those skilled in the art. A suitable method involves use of LDA and diethyl carbonate or diethyl pyrocarbonate. It was observed that carboxylation easily occurred on unprotected 8-methoxy-2,3,4,5-tetrahydro-1H-1-benzazepine-2-one (3A) while the same reaction failed when 1-ethyl-8-methoxy-2,3,4,5-tetrahydro-1H-1-benzazepine-2-one was employed as a starting material. 3(R,S)-Ethoxycarbonyl-8-methoxy-2,3,4,5-tetrahydro-1H-1-benzazepine-2-one (4A) was protected on the hetero-atom using iodoethane as an alkylating agent in a cesium carbonate mediated reaction. A saponification of 1-ethyl-3(R,S)-ethoxycarbonyl-8-methoxy-2,3,4,5-tetrahydro-1H-1-benzazepine-2-one (5A) in basic reaction conditions afforded the desired NCE, 3(R,S)-carboxyl-1-ethyl-8-methoxy-2,3,4,5-tetrahydro-1H-1-benzazepine-2-one (6A).

When 3(R,S)-ethoxycarbonyl-8-methoxy-2,3,4,5-tetrahydro-1H-1-benzazepine-2-one (4A) was treated with two equivalents of sodium hydride as a base and iodoethane as an alkylating reagent dialkylation was observed resulting in a formation of 1,3-diethyl-3(R,S)-ethoxycarbonyl-8-methoxy-2,3,4,5-tetrahydro-1H-1-benzazepine-2-one (7A) as illustrated in Scheme 2. Further saponification in basic reaction conditions produced 1,3-diethyl-3(R,S)-carboxyl-8-methoxy-2,3,4,5-tetrahydro-1H-1-benzazepine-2-one (8A).

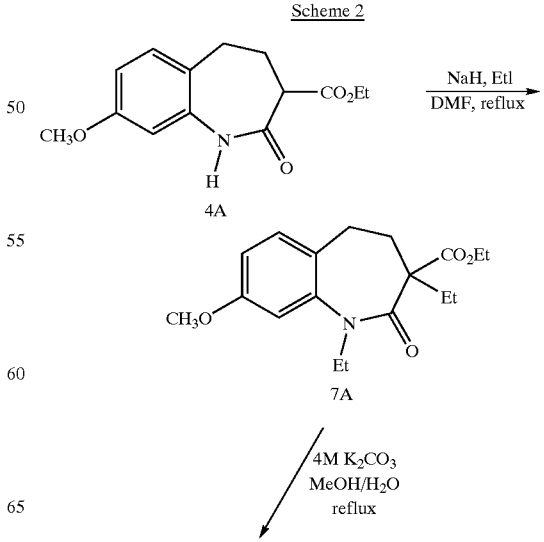

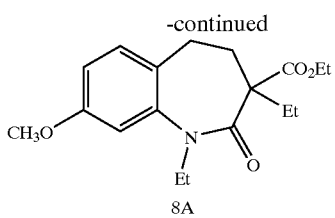

8A

As shown in Scheme 3, 8-methoxy-2,3,4,5-tetrahydro-1H-1-benzazepine-2-one (3A) was alkylated using iodoethane as an alkylating reagent and one equivalent of sodium hydride as a base to provide 1-ethyl-8-methoxy-2,3,4,5-tetrahydro-1H-1-benzazepine-2-one (9A). A bromination in methanol at ambient temperature using bromine as a brominating agent afforded exclusively 7- bromo regioisomer (10A) which was transformed further employing a catalytic cross coupling methodology. This coupling reaction was conveniently carried out by use of 4-methylpiperazine as a reagent, BINAP as a chelating reagent, palladium acetate as a catalyst in the presence of cesium carbonate as a base.

Syntheses of 3(R,S)-carboxyl-1-ethyl-8-methoxy-2,3,4,5-tetrahydro-1H-1-benzazepine-2-one (6A) and 3(R,S)-carboxyl-1-ethyl-8-methoxy-7-piperazinyl-2,3,4,5-tetrahydro-1H-1-benzazepine-2-one (6B) have been designed in such a manner that a common route proceeds via the intermediacy of 8-methoxy-2,3,4,5-tetrahydro-1H-1-benzazepine-2-one (3A). In this particular reaction sequence as illustrated in Scheme 4, 8-methoxy-2,3,4,5-tetrahydro-1H-1-benzazepine-2-one (3A) was transformed to the 3(R,S)-ethoxycarbonyl (2B) and 3-tert-butoxycarbonyl (1B) derivatives of their common precursor using diethyl pyrocarbonate or di-tert-butyl carbonate, respectively. 3(R,S)-tert Butoxycarbonyl-8-methoxy-2,3,4,5-tetrahydro-1H-1-benzazepine-2-one (1B) was chosen as a preferable intermediate over its ethyl ester counterpart due to a higher yield in the relevant carboxylation step. Furthermore, it is a common knowledge that tert-butyl ester groups are easier to be removed than ethyl ester groups. A protection of the heteroatom was effected by using iodoethane as an alkylating reagent in a cesium carbonate mediated reaction.

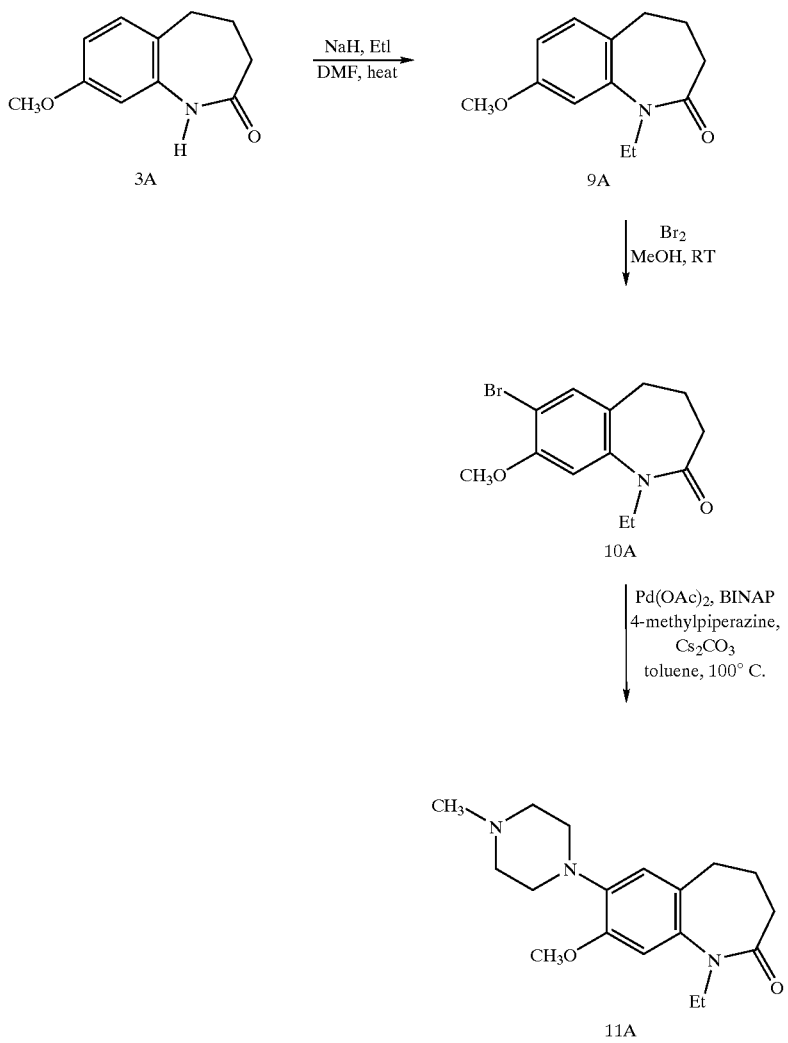

Scheme 4

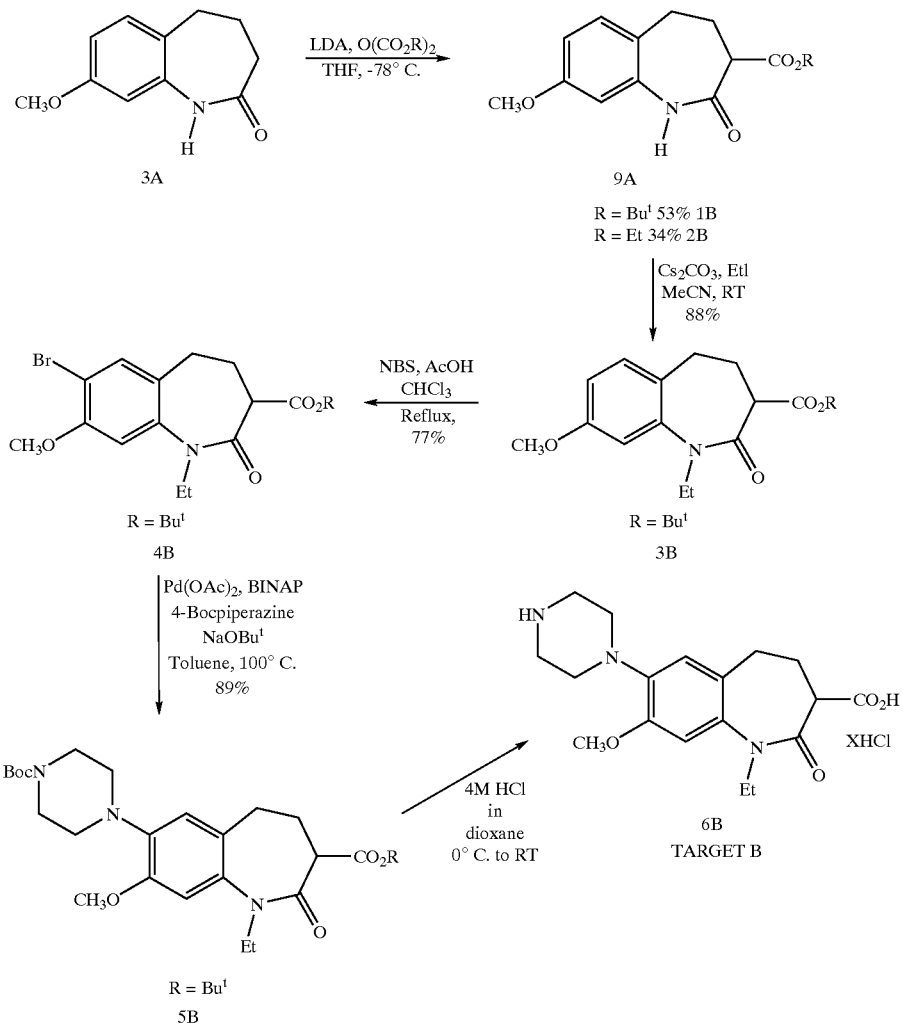

1-tert-Butoxycarbonyl-3(R,S)-tert-butoxycarbonyl-8-methoxy-2,3,4,5-tetrahydro-1H-1-benzazepine-2-one was obtained in a low yield as a side product in a synthesis of 3(R,S)-tert-butoxycarbonyl-8-methoxy-2,3,4,5-tetrahydro-1H-1-benzazepine-2-one. To improve the yield in a synthesis of 1-tert-butoxycarbonyl-3(R,S)-tert-butoxycarbonyl-8-methoxy-2,3,4,5-tetrahydro-1H-1-benzazepine-2-one, 3(R,S)-tert-butoxycarbonyl-8-methoxy-2,3,4,5-tetrahydro-1H-1-benzazepine-2-one was exposed to di-tert-butyl dicarbonate in a cesium carbonate or sodium hydride mediated reaction. Indeed, the desired 1-tert-butoxycarbonyl-3(R,S)-tert-butoxycarbonyl-8-methoxy-2,3,4,5-tetrahydro-1H-1-benzazepine-2-one was obtained in good yield.

A synthesis of 3-tert-butoxycarbonyl-1-(3-fluorobenzyl)-8-methoxy-2,3,4,5-tetrahydro-1H-1-benzazepine-2-one demonstrated that substituted 1-benzazepine-2-ones are appropriate substrates for benzylic alkylation on the heteroatom.

A bromination of 3(R,S)-tert-butoxycarbonyl-1-ethyl-8-methoxy-2,3,4,5-tetrahydro-1H-1-benzazepine-2-one (3B) using N-bromosuccinimide as a brominating reagent in the presence of a catalytic amount of acetic acid produced exclusively 7-bromo regioisomer (4B). The same bromination procedure was used to synthesize the 7-bromo derivatives of 3(R,S)-tert-butoxy carbonyl-1-(3-fluorobenzyl)-8-methoxy-2,3,4,5-tetrahydro-1H-1-benzazepine-2-one and 3(R,S)-tert-butoxycarbonyl-8-methoxy-2,3,4,5-tetrahydro-1H-1-benzazepine-2-one. A formation of 7-bromo-3(R,S)-tert-butoxycarbonyl-8-methoxy-2,3,4,5-tetrahydro-1H-1-benzazepine-2-one indicated that a bromination of 1-benzazepine-2-one skeleton could be performed although the heteroatom is unprotected. Bromination of 8-methoxy-2,3,4,5-tetrahydro-1H-1-benzazepine-2-one with NBS and a catalytic amount of benzoyl peroxide (BPO) in carbon tetrachloride resulted in 7-bromo-8-methoxy-2,3,4,5-tetrahydro-1H-1-benzazepine-2-one.

Conversion of 7-bromo-3(R,S)-tert-butoxy-carbonyl-1-ethyl-8-methoxy-2,3,4,5-tetrahydro-1H-1-benzazepine-2-one (4B) to the requisite 7-piperazinyl derivative can be achieved by a number of cross coupling methodologies familiar to those skilled in the art including that described by L. Buchwald, et al, Tet. Lett. (1998) 39, 5327–5330. The chelating ligand BINAP in combination with palladium acetate forms a highly effective catalyst system for the coupling of anilines with aryl bromides. This catalyst system is effective in coupling reactions involving a variety of substrates, including electron poor anilines or electron-rich aryl bromides. In addition, this cross coupling reaction tolerates a high degree of steric congestion at both aniline and aryl bromide. We have employed the latter cross coupling methodology for the coupling of piperazine/protected piperazine with an electron rich arylbromide moiety, which probably exhibits steric congestion at the reactive site imposed by a bulky ortho methoxy group. Precisely, a cross coupling of 7-bromo-3(R,S)-tert-butoxycarbonyl-1-ethyl-8-methoxy-2,3,4,5-tetrahydro-1H-1-benzazepine-2-one (4B) with 1-tert-butoxycarbonyl-piperazine in the presence of BINAP as a chelating reagent, palladium acetate as a catalyst and sodium tert-butoxide as a base gave 3(R,S)-tert-butoxycarbonyl-7-[(4-tert-butoxycarbonyl-piperazine)-1-yl]-1-ethyl-8-methoxy-2,3,4,5-tetrahydro-1H-1-benzazepine-2-one (5B) as a penultimate precursor of the desired NCE. Deprotection of piperazine moiety of the molecule and removal of tert-butyl ester group in a one pot reaction using a concentrated solution of hydrochloric acid in dioxane provided 3(R,S)-carboxyl-1-ethyl-8-methoxy-7-piperazinyl-2,3,4,5-tetrahydro-1H-1-benzazepine-2-one hydrochloride salt (6B). Furthermore, utilization of 1-benzyloxycarbonylpiperazine as a secondary amine component in the former cross coupling reaction offered 7-[(4-benzyloxycarbonyl)piperazin-1-yl]-3(R,S)-tert-butoxycarbonyl-1-ethyl-8-methoxy-2,3,4,5-tetrahydro-1H-1-benzazepine-2-one when 7-bromo-3(R,S)-tert-butoxycarbonyl-1-ethyl-8-methoxy-2,3,4,5-tetrahydro-1H-1-benzazepine-2-one was used as a starting compound. Thus, a strategy of cross coupling of a piperazine/protected piperazine with an electron rich heteroarylbromide has considerable flexibility to vary structure and should be a versitile route to the preparation of biologically active anti-infectives using automatic parallel syntheses. A synthesis of 1-ethyl-8-methoxy-7-piperazinyl-2,3,4,5-tetrahydro-1H-1-benzazepine-2-one hydrochloride was executed via 7-[(4-tert-butoxycarbonylpiperazin)-1-yl]-1-ethyl-8-methoxy-2,3,4,5-tetrahydro-1H-1-benzazepine-2-one as an immediate precursor.

7-[(4-Benzyloxycarbonyl)piperazin-1-yl]-3-tert-butoxycarbonyl-1-(3-fluorobenzyl)-8-methoxy-2,3,4,5-tetrahydro-1H-1-benzazepine-2-one has been thus far the most complex ring system in our development of new strategies for syntheses of the 1-benzazepine anti-infectives.

When 3(R,S)-tert-butoxycarbonyl-1-ethyl-8-methoxy-2,3,4,5-tetrahydro-1H-1-benzazepine-2-one (3B) was treated with N-bromosuccunimide in the presence of a catalytic amount of benzoyl peroxide at elevated temperature, a bromination probably occurred at the benzylic position as illustrated in Scheme 5. A consequent elimination of HBr afforded 3(R,S)-tert-butoxycarbonyl-1-ethyl-8-methoxy-2,3-dihydro-1H-1-benzazepine-2-one (7B).

Scheme 5

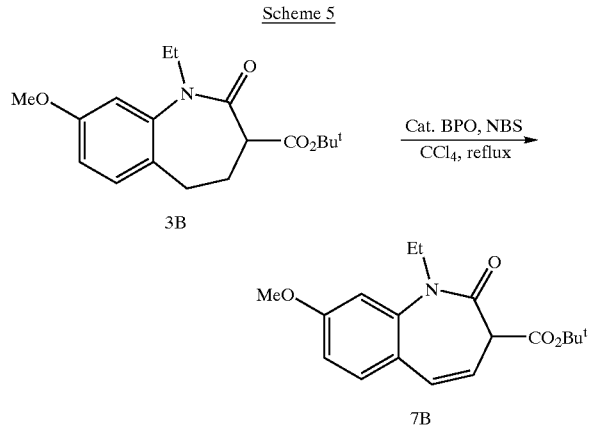

Several derivatives of 7-bromo-3(R,S)-tert-butoxycarbonyl-1-ethyl-8-methoxy-2,3,4,5-tetrahydro-1H-1-benzazepine-2-one (4B) were prepared as depicted on Scheme 6. Removal of an ester group using concentrated trifluoroacetic acid at ambient temperature afforded 7-bromo-3(R,S)-carboxyl-1-ethyl-8-methoxy-2,3,4,5-tetrahydro-1H-1-benzazepine-2-one (8B). A cross coupling reaction of 7-bromo-3(R,S)-tert-butoxycarbonyl-1-ethyl-8-methoxy-2,3,4,5-tetrahydro-1H-1-benzazepine-2-one (4B) with piperazine in the presence of BINAP as a chelating reagent, palladium acetate as a catalyst and cesium carbonate as a base gave 3(R,S)-tert-butoxy carbonyl-1-ethyl-8-methoxy-7-piperazinyl-2,3,4,5-tetrahydro-1H-1-benzazepine-2-one (9B). A low yield in this cross coupling reaction was due to a formation of 1,4-di-[(3(R,S)-tert-butoxycarbonyl-1-ethyl-8-methoxy-2-oxo-2,3,4,5-tetrahydro-1H-1-benzazepine)-7-yl]-piperazine (10B). Saponification of 1,4-di-[(3(R,S)-tert-butoxycarbonyl-1-ethyl-8-methoxy-2-oxo-2,3,4,5-tetrahydro-1H-1-benzazepine)-7-yl]-piperazine using concentrated trifluoroacetic acid as a deprotecting reagent produced 1,4-di-[(3(R,S)-carboxyl-1-ethyl-8-methoxy-2-oxo-2,3,4,5-tetrahydro-1H-1-benzazepine)-7-yl]-piperazine (11B).

Scheme 6

8B

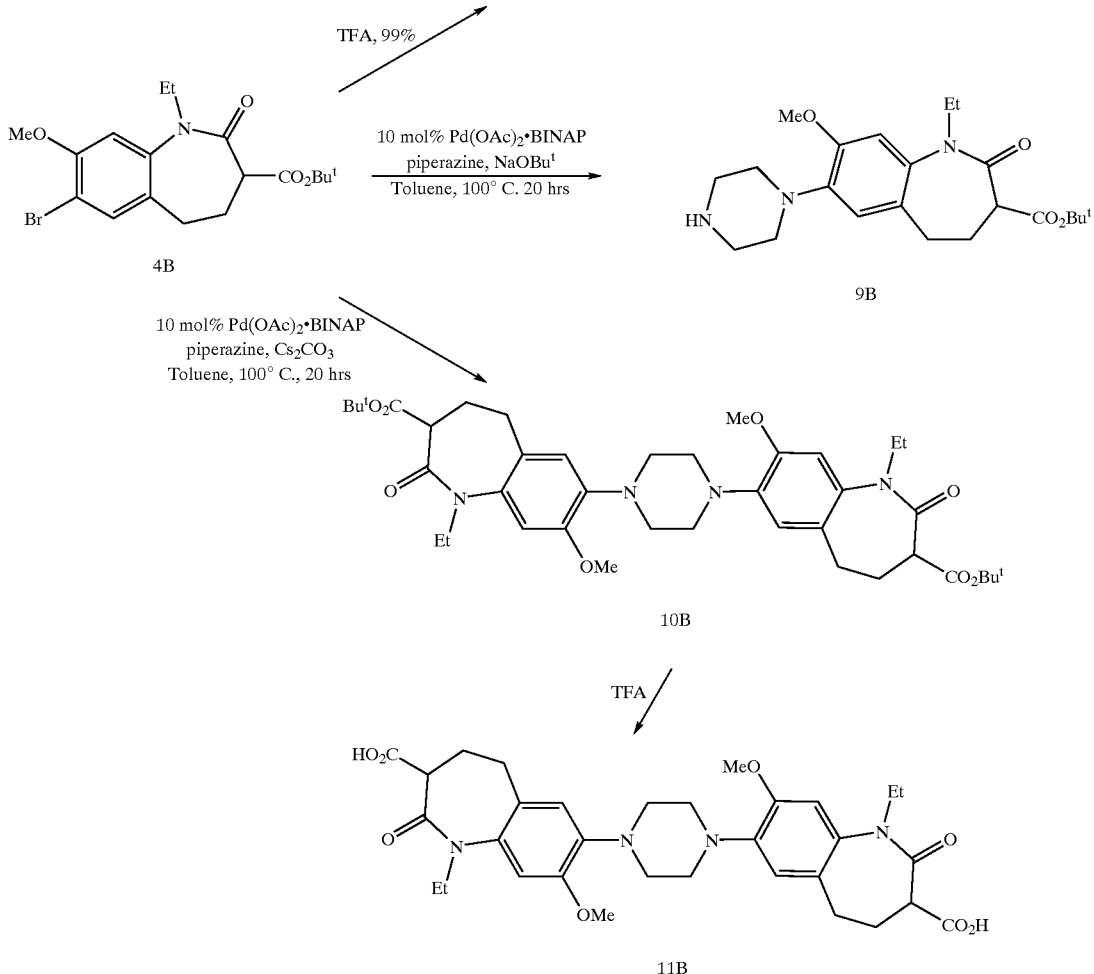

When 7-bromo-3(R,S)-tert-butoxycarbonyl-1-ethyl-8-methoxy-2,3,4,5-tetrahydro-1H-1-benzazepine-2-one was treated with bromine in MeOH at ambient temperature, bromination occurred at 3-position of the 1-benzazepine-2-one ring system. In addition, a transesterification due to the presence of methanol was observed which resulted in a formation of 7-bromo-3(R,S)-methoxycarbonyl-1-ethyl-8-methoxy-2,3,4,5-tetrahydro-1H-1-benzazepine-2-one.

Replacement of an ester functional group by an aminocarbonyl group in the substituted 1-benzazepine-2-one system has been succesfully employed in a synthesis of 7-bromo-3(R,S)-N-(tert-butyl)aminocarbonyl-1-ethyl-8-methoxy-2,3,4,5-tetrahydro-1H-1-benzazepine-2-one. The latter compound was synthesized by a coupling reaction of 7-bromo-3(R,S)-carboxyl-1-ethyl-8-methoxy-2,3,4,5-tetrahydro-1H-1-benzazepine-2-one with tert-butyl amine using 1-[3-(dimethylamino)propyl]-3-ethylcarbodiimide hydrochloride (EDCI)/1-hydroxybenzotriazole (HOBT) and triethylamine as reaction mediators. A series of N-terminal groups of the aminocarbonyl functionality are under investigation. This amide bond formation offers a possibility of the use of an appropriately protected amino acid as an amino component. In addition, it is perceived that this coupling strategy could be used to introduce a peptidomimetic side chain on 3-position of the 1-1-benzazepine-2-one ring system including hydrophobic spacers, such as substituted 4-aminobenzoyl group.

EXAMPLES

The following specific examples are provided for the purpose of further illustration only and are not intended to limit the disclosed invention.

Melting points were measured with Mel-Temp melting point apparatus and were uncorrected.

$^1$H and $^{13}$C NMR spectra were recorded on Varian VXR 4000 in deuterochloroform(CDCl$_3$) with chloroform as an internal reference or in deuterated DMSO (DMSO-d$_6$) with DMSO as an internal reference unless noted otherwise. $^1$H and $^{13}$C chemical shift assignments are based on detailed analysis of two dimensional or decoupled spectra when necessary. $^1$H spectra were recorded at 400, usually 3.7 sec. acquisition time. $^{13}$C spectra were recorded at 100 MHz, 1.1 sec acquisition time. DEPT spectra were recorded at 400 MHz using 135 degree $^1$H read pulse, usually 256 or 512 transients, 4 sec relaxation delay containing homospoil pulse.

Samples analyzed by GC-MS were acquired using Finnigan 4500 single quadrropole mass spectrometer utilizing electron impact (EI) ionization; samples analyzed using direct probe EI ionization or fast atom bombardment (FAB) ionization were acquired using a VG 70 SQ high resolution double-focusing magnetic sector instrument (EB geometry); and samples analyzed by electrospray ionization were acquired on a VG Trio 3 triple quadropole mass spectrometer.

TLC was performed on EM Reagents precoated Silica Gel 60 F-254 analytical plates (0.25 mm). Normal phase flash column chromatography was performed on ICN Silica, 60 Å (18–32 Mesh, 32–63 Mesh). Normal phase gravity chromatography was performed on ICN Silica, 60 Å (63–200 Mesh). Purity and homogeneity of all materials were determined chromatographically, from MS, $^1$H and $^{13}$C NMR or combustion analysis. THF was distilled from sodium-benzophenone ketyl. Other reagents were obtained commercially and used as received unless otherwise specified. All reactions were performed under a static argon or nitrogen atmosphere in flame/oven dried glassware. Elemental analyses were performed by QTI Whitehouse, N.J.

Intermediate 1

7-Methoxy-1-tetralone Oxime

Method A

A mixture of 7-methoxy-1-tetralone (500 mg, 2.84 mmol), hydroxylamine sulfate (492 mg, 2.99 mmol) and anhydrous pyridine (20 ml) was heated at 100° C. under argon. The course of the reaction was monitored by TLC (THF 3: n-hexane 7). After 5.5 hours the reaction mixture was allowed to cool to room temperature and poured on crushed ice (30 ml). pH of the resulting solution was adjusted to 3.5 with conc. solution of HCl at 0° C. After cooling the resulting suspension in an ice bath for 4 hours, the precipitate was collected by filtration to yield first crop of the crude product. The corresponding filtrate was extracted three times with chloroform, the combined organic extracts washed with brine and dried over anhydrous magnesium sulfate. After removing the drying agent the solution was evaporated under reduced pressure to dryness. Thus obtained second crop was combined with first crop to yield crude 7-methoxy-1-tetralone oxime (382 mg) that was dried in a desiccator over $P_2O_3$ under vacuum at ambient temperature for 12 hours. The crude product was purified by silica gel gravity chromatography using 20% THF in n-hexane as an eluent to give 331 mg (61% yield) of white crystalline product.

Method B

The title compound was prepared by the same procedure as stated above: Reaction of 7-methoxy-1-tetralone (10.00 g, 56.8 mmol) with $(H_2NOH)_2H_2SO_4$ (9.84 g, 59.8 mmol) in anhydrous pyridine (200 mL) provided a crude product which was recrystallized from a solvent mixture of hexane/chloroform (1:1). The final product was obtained as a white crystalline product (9.43 g, 87%).

M.P.=8°–82° C. $C_{11}H_{13}NO_2$ (191.23): MS (FAB, NBA) m/e 192 (M+H)$^+$.

This product was also analyzed by $^1$H and $^{13}$C NMR. The corresponding NMR spectra were consistent with the structure of the anticipated product.

Example 2

8-Methoxy-2,3,4,5-tetrahydro-1H-1-benzazepine-2-one

Method A

To a vigorously stirred neat methanesulfonic acid, (25 ml) phosphorus pentoxide (2.83 g, 10 mmol) was added under a stream of argon. The resulting reaction mixture was vigorously stirred and heated at 100° C. for an hour. After the reaction mixture was allowed to cool to ambient temperature 7-methoxy-1-tetralone oxime (300 mg, 1.57 mmol) was added as a dry powder under a stream of argon. The resulting reaction mixture turned immediately from colorless to dark brown solution that was vigorously stirred and heated at 100° C. for 30 min. After cooling the reaction mixture at 0° C. for 30 min it was neutralized with a saturated solution of sodium hydrogencarbonate. The resulting suspension was stirred at 0° C. for 4 hours and the precipitate collected by filtration to give first crop of a crude product. The corresponding filtrate was extracted three times with chloroform, the combined organic extracts washed with brine and dried over anhydrous magnesium sulfate. After removing the drying agent the solution was evaporated under reduced pressure and thus obtained second crop was combined with first crop to yield 271 mg of a crude product. A silica gel flash chromatography using 20% THF in n-hexane as eluent produced 210 mg (70% yield) of beige crystalline product.

Method B

The title compound was prepared by the same procedure as stated above. The reaction of 7-methoxy-1-tetralone oxime (9.00 g, 47.1 mmol) and $P_2O_5$ (11.00 g) in methanesulfonic acid (100 mL) gave a crude product which was purified by flash chromatography on silica column with EtOAc/hexane (7:3) as an eluent. Purification procedure provided 6.56 g (73%) of the desired intermediate and 0.27 g of the recovered starting material.

M.P.=105°–106° C. $C_{11}H_{13}NO_2$ (191.23); MS (EI+) m/e 191 (M)+.

This product was also analyzed by $^1$H and $^{13}$C NMR. The corresponding NMR spectra were consistent with the structure of the anticipated product.

Example 3

3(R,S)-Ethoxycarbonyl-8-methoxy-2,3,4,5-tetrahydro-1H-1-benzazepine-2-one

Method A

To a solution of 8-methoxy-2,3,4,5-tetrahydro-1H-1-benzazepine-2-one (300 mg, 1.6 mmol) in THF (25 ml) at −78° C. was slowly added a solution of LDA (1.8 ml, 3.52 mmol, 2M solution of LDA in heptane/THF/ethylbenzene). The resulting reaction mixture was vigorously stirred at −78° C. under stream of argon for 30 min and then at −5° C. for 45 min. After this reaction period a solution of diethyl carbonate in THF (3.4 ml, c=136 mg/ml.) was added at −5° C. and the reaction mixture was stirred at −5° C. for 20 min and allowed to warm to ambient temperature. The reaction mixture was stirred for three hours before quenching with saturated aqueous ammonium chloride. Extraction of aqueous phase with a solvent mixture of THF and ether (20% THF in ether), washing the combined extracts with saturated solution of ammonium chloride and brine, drying and solvent evaporation gave a beige crude product. A flash chromatography of a crude product on silica gel column with 30% THF in n-hexane as an eluent produced 119 mg (28%) of a white solid.

Method B

An oven-dried flask was charged with 8-methoxy-2,3,4,5-tetrahydro-1H-1-benzazepine-2-one (0.976 g, 5.10 mmol) and anhydrous THF (30 mL). 1.9 M LDA in heptane/THF/ethylbenzene (5.90 mL, 11.24 mmol) was added dropwise via syringe at −78° C. under the protection of argon. The reaction mixture was allowed to warm up to room temperature, stirred for 1.5 hrs and cooled down to −78° C. again. A solution of diethyl pyrocarbonate (0.93 mL, 6.12 mmol) in anhydrous THF (5 mL) was added dropwise. After being stirred at −78° C. for 2 hrs and at room temperature for 1.5 hrs, the reaction mixture was quenched with saturated aqueous solution of $NH_4Cl$ (3 mL) and evaporated under reduced pressure. The residue was dissolved in dichloromethane, washed with water and dried over $MgSO_4$. A purification of the crude product by flash chromatography on silica column with EtOAc/hexane (7:3) as an eluent provided 0.45 g (34%) of the desired compound as an oil that gradually crystallized at 0° C. over an extended period of time.

M.P.=89–91° C. $C_{14}H_{18}NO_4$ (264.29) MS (EI+) m/e 264 (M)+.

This product was also analyzed by $^1H$ and $^{13}C$ NMR. The corresponding NMR spectra were consistent with the structure of the anticipated product.

Example 4

3(R,S)-Ethoxycarbonyl-1-ethyl-8-methoxy-2,3,4,5-tetrahydro-1H-1-benzazepine-2-one A suspension of 3(R,S)-ethoxycarbonyl-8-methoxy-2,3,4,5-tetrahydro-1H-1-benzazepine-2-one (0.45 g, 1.71 mmol), ethyl iodide (0.41 mL, 5.1 mmol) and $Cs_2CO_3$ (1.672 g, 5.1 mmol) in acetonitrile (5 mL) was stirred at room temperature for 6 hrs. The reaction mixture was filtered and the solid was washed with acetonitrile. The combined filtrate and washer were evaporated under reduced pressure. The crude product was purified by flash chromatography on a short silica gel column using EtOAc/hexane (3:7) as an eluent. The title compound (0.241 g, 48%) was obtained as an oil.

B.P.>200° C. $C_{16}H_{21}NO_4$ (291.35); MS (EI) m/e 291 $(M^+)$.

This product was also analyzed by $^1H$ and $^{13}C$ NMR. The corresponding NMR spectra were consistent with the structure of the anticipated product.

Example 5

3(R,S)-Carboxyl-1-ethyl-8-methoxy-2,3,4,5-tetrahydro-1H-1-benzazepine-2-one

A solution of 3(R,S)-ethoxycarbonyl-1-ethyl-8-methoxy-2,3,4,5-tetrahydro-1H-1-benzazepine-2-one (90 mg, 0.31 mmol) in 1M KOH in 90% MeOH (1.5 mL) was refluxed overnight. The course of the reaction was monitored by TLC. Then, pH of the reaction mixture was adjusted to 4.0 with HCl/MeOH solution (10% (V) conc. HCl in MeOH), filtered and evaporated. The residue was dissolved with DCM (30 mL), dried over $MgSO_4$, filtered and evaporated to dryness. Thus obtained solid residue was washed with hexane and dried over $P_2O_5$ in vacuum. The desired product (73 mg, 90%) was obtained as white powder.

M.P=120–121° C. $C_{14}H_{17}NO_4$ (263.10); MS (EI) m/e 263 $(M^+)$.

This product was also analyzed by $^1H$ and $^{13}C$ NMR. The corresponding NMR spectra were consistent with the structure of the anticipated product.

Example 6

1,3-Diethyl-3(R,S)-ethoxycarbonyl-8-methoxy-2,3,4,5-tetrahydro-1H-1-benzazepine-2-one A mixture of 3(R,S)-ethoxycarbonyl-8-methoxy-2,3,4,5-tetrahydro-1H-1-benzazepine-2-one (260 mg, 1 mmol), NaH (60 mg, 2.5 mmol), EtI (400 µl, 5 mmol) and anhydrous DMF (25 ml) was stirred at room temperature under argon for 18 hrs. After this reaction period the reaction mixture was evaporated under reduced pressure to dryness. Ice cold water was added and the resulting emulsion/suspension was stirred at 0° C. for 20 min. Organic phase was extracted with a mixture of THF and ether (20% THF in ether) and the combined extracts were washed with 2% solution of HCl and brine. After drying over magnesium sulfate the solution was evaporated to dryness. Thus obtained crude product was purified by flash chromatography to yield 230 mg (73%) of white solid.

M.P.=amorphous compound; $C_{18}H_{25}NO_4$ (319.41); MS (EI+) m/e 319 $(M)^+$.

This product was also analyzed by $^1H$ and $^{13}C$ NMR. The corresponding NMR spectra were consistent with the structure of the anticipated product.

Example 7

3(R,S)-Carboxyl-1,3-diethyl-8-methoxy-2,3,4,5-tetrahydro-1H-1-benzazepine-2-one

A mixture of 3(R,S)-ethoxycarbonyl-1,3-diethyl-8-methoxy-2,3,4,5-tetrahydro-1H-1-benzazepine-2-one (200 mg, 0.63 mmol), potassium carbonate (3.5 g, 25 mmol), and 50% methanol (20 ml) was refluxed for 48 hrs. The resulting reaction mixture was cooled at 0° C. and pH adjusted to 3.5 with a methanolic solution of HCl (30% (V) conc. HCl in methanol). The precipitate was collected by filtration, the filter cake washed with methylene chloride and the corresponding filtrate evaporated to dryness. This crude product was purified by gravity chromatography on Floresil using gradient elution starting with 5% methanol in chloroform followed by 10% methanol in chloroform. 139 mg (76%) of white amorphous solid was obtained.

M.P.: amorphous compound; $C_{16}H_{21}NO_4$ (291.35); MS (FAB, NBA) m/e 292 $(M+H)^+$.

This product was also analyzed by $^1H$ and $^{13}C$ NMR. The corresponding NMR spectra were consistent with the structure of the anticipated product.

Example 8

1-Ethyl-8-methoxy-2,3,4,5-tetrahydro-1H-1-benzazepine-2-one

A mixture of 8-methoxy-2,3,4,5-tetrahydro-1H-1-benzazepine-2-one (2.6 g, 13.6 mmol), NaH (648 mg, 27 mmol) and iodoethane (3 ml, 37 mmol) in anhydrous DMF (50 ml) was vigorously stirred and heated at 100° C. for one hour. The reaction mixture was evaporated under reduced pressure to dryness and the residue dissolved in 100 ml ice-cold water. The resulting brown emulsion was extracted three times with chloroform, the combined extracts were washed with 2% solution of HCl and brine. The organic phase was treated with decolorizing carbon, stirred at room temperature for an hour and filtered through Celite. After drying over anhydrous magnesium sulfate the filtrate was evaporated to dryness. The residual oil was purified by gravity column chromatography on silica gel using 30% THF in n-hexane as an eluent to yield 2.2 g (74%) of the desired compound as a pale yellow oil.

B.P.>200° C. $C_{13}H_{17}NO_2$ (219.29); MS (FAB, NBA) m/e 318 $(M+H)^+$.

This product was also analyzed by $^1H$ and $^{13}C$ NMR. The corresponding NMR spectra were consistent with the structure of the anticipated product.

Example 9

7-Bromo-1-ethyl-8-methoxy-2,3,4,5-tetrahydro-1H-1-benzazepine-2-one

A mixture of 1-ethyl-8-methoxy-2,3,4,5-tetrahydro-1H-1-benzazepine-2-one (200 mg, 0.91 mmol) and bromine (581 mg, 3.64 mmol) in anhydrous methanol was stirred at room temperature for an hour. After this reaction period the reaction mixture was diluted with 150 ml of methanol and treated with decolorizing carbon. After stirring the reaction mixture at ambient temperature for an hour it was filtered through celite, evaporated under reduced pressure to dryness. The crude residue was dissolved in ice-cold water and extracted with a solvent mixture of THF and ether (20% THF in ether). The combined organic extracts were washed with 5% solution of sodium hydrogencarbonate and brine. After drying the organic phase over magnesium sulfate it was evaporated to dryness and the crude product purified by gravity chromatography using 30%. THF in n-hexane as an eluent. 220 mg (81%) of pure product was obtained as a white crystalline solid.

M.P.=133–135° C.; $C_{13}H_{16}BrNO_2$ (298.18); MS (EI$^+$) m/e 298 (M)$^+$.

This product was also analyzed by $^1$H and $^{13}$C NMR. The corresponding NMR spectra were consistent with the structure of the anticipated product.

Example 10

1-Ethyl-8-methoxy-7-[(4-methylpiperazin)-1-yl)]-2,3,4,5-tetrahydro-1H-1-benzazepine-2-one A mixture of 7-bromo-1-ethyl-8-methoxy-2,3,4,5-tetrahydro-1H-1-benzazepine-2-one (200 mg, 0.67 mmol), BINAP (50 mg, 0.08 mmol), palladium acetate (12 mg, 0.053 mmol), cesium carbonate (238 mg, 0.73 mmol) in 3 ml of anhydrous toluene was heated at 100° C. under strictly inert atmosphere for 24 hours. After this reaction period the reaction mixture was diluted with 100 ml of methanol and filtered through Celite. The filtrate was evaporated to dryness and the crude product purified by flash chromatography on silica gel column using 5- methanol as an eluent. 118 mg (56%) of pure product was obtained as an off-white crystalline solid.

M.P.=138–140° C. $C_{18}H_{27}N_3O_2$ (317.44); MS (FAB, NBA) m/e 318 (M+H)$^+$.

This product was also analyzed by $^1$H and $^{13}$C NMR. The corresponding NMR spectra were consistent with the structure of the anticipated product.

Example 11

3(R,S)-tert-Butoxycarbonyl-8-methoxy-2,3,4,5-tetrahydro-1H-1-benzazepine-2-one

An oven-dried flask was charged with 8-methoxy-2,3,4,5-tetrahydro-1H-1-benzazepine-2-one (0.956 g, 5.00 mmol) and anhydrous THF (30 mL). 1.9 M LDA in heptane/THF/ethylbenzene (5.79 mL, 11.00 mmol) was added dropwise at −78° C. under argon. The reaction mixture was then allowed to warm to room temperature, stirred for 1.5 hrs and cooled to −78° C. again. A solution of di-tert-butyl dicarbonate (1.09 g, 5.00 mmol) in anhydrous THF (5 mL) was added dropwise through a syringe. After stirring the reaction mixture at −78° C. for 1.5 hrs, it was allowed to warm to ambient temperature, quenched with saturated aqueous solution of NH$_4$Cl (5 mL) and evaporated to dryness under reduced pressure. The crude product was dissolved in dichloromethane, washed with water and dried over anhydrous Na$_2$SO$_4$. Purification by flash chromatography on silica column eluted with EtOAc/n-hexane (3:7–5:5) provided the desired compound (0.537 g, 53%) as white powder and recovered starting material (0.294 g, conversion 69%).

M.P.: 145–147° C.; $C_{16}H_{21}NO_4$ (291.35); MS (FAB, NBA) m/e 292 (M+H)$^+$.

This product was also analyzed by $^1$H and $^{13}$C NMR. The corresponding NMR spectra were consistent with the structure of the anticipated product.

Example 12

3(R,S)-tert-Butoxycarbonyl-1-ethyl-8-methoxy-2,3,4,5-tetrahydro-1H-1-benzazepine-2-one A suspension of 3(R,S)-tert-butoxycarbonyl-8-methoxy-2,3,4,5-tetrahydro-1H-1-benzazepine-2-one (3.645 g, 12.51 mmol), ethyl iodide (2.01 mL, 25.02 mmol) and Cs$_2$CO$_3$ (8.153 g, 25.02 mmol) in acetonitrile (35 mL) was stirred at room temperature for 6 hrs. The reaction mixture was evaporated to dryness, the residue dissolved in water and extracted with DCM. The organic layer was washed with water, dried over Na$_2$SO$_4$, filtered and evaporated to dryness. The solid residue was washed with n-hexane and dried in vacuum. The desired compound (3.50 g, 88%) was obtained as white crystalline powder.

M.P.: 132–133° C.; $C_{18}H_{25}NO_4$ (319.40); MS (FAB, NBA) m/e 320 (M+H)$^+$.

This product was also analyzed by $^1$H and $^{13}$C NMR. The corresponding NMR spectra were consistent with the structure of the anticipated product.

Example 13

7-Bromo-3(R,S)-tert-butoxycarbonyl-1-ethyl-8-methoxy-2,3,4,5-tetrahydro-1H-1-benzazepine-2-one A solution of 3(R,S)-tert-butoxycarbonyl-1-ethyl-8-methoxy-2,3,4,5-tetrahydro-1H-1-benzazepine-2-one (3.38 g, 10.58 mmol) and N-bromosuccinimide (2.072 g, 11.64 mmol) in acetic acid (2.5 mL) and chloroform (25 mL) was heated at reflux for 2 hrs. The reaction mixture was diluted with chloroform (25 mL), washed with saturated aqueous solution of NaHCO$_3$ and water, dried over Na$_2$SO$_4$, filtered and evaporated to dryness. Purification of the crude product by flash chromatography on silica gel column eluted with EtOAc/hexane (3:7) provided the desired compound (3.25 g, 77%) as white powder.

M.P.:131–132° C. $C_{18}H_{24}BrNO_4$ (398.30); MS (EI) m/e 398 (M$^+$).

This product was also analyzed by $^1$H and $^{13}$C NMR. The corresponding NMR spectra were consistent with the structure of the anticipated product.

Example 14

3(R,S)-tert-Butoxycarbonyl-7-[(4-tert-butoxycarbonyl-piperazin)-1-yl]-1-ethyl-8-methoxy-2,3,4,5-tetrahydro-1H-1-benzazepine-2-one An oven-dried flask was charged with 7-bromo-3(R,S)-tert-butoxycarbonyl-1-ethyl-8-methoxy-2,3,4,5-tetrahydro-1H-1-benzazepine-2-one (1.20 g, 3.00 mmol), tert-butyl-1-piperazinecarboxylate (0.67 g, 3.60 mmol), Pd(OAc)$_2$ (33.6 mg, 0.150 mmol, 5 mol %), BINAP (140.2 mg, 0.225 mmol) and purged with argon for 5 min. Anhydrous toluene (15 mL) was added through a syringe, resulted in a clear yellowish solution. Sodium tert-butoxide (0.40 g, 4.2 mmol) was added in one portion as a dry powder. After purging with argon for 3 min, the reaction mixture was heated and vigorously stirred at 100° C. for 2 hrs. The course of the reaction was monitored by TLC. The reaction mixture was diluted with DCM (20 mL), washed with water, dried over anhydrous Na$_2$SO$_4$, filtered and evaporated to dryness. The crude product was purified by flash chromatography on silica column eluted with MeOH/DCM (1:19). Thus obtained solid was further purified by crystallization from chloroform/EtOAc (1:3) to afford the desired compound (1.34 g, 89%) as a white crystalline product.

M.P.: 135–137° C. $C_{27}H_{41}N_3O_6$ (503.65); MS (FAB) m/e 504 (M+1)$^+$.

This product was also analyzed by $^1$H and $^{13}$C NMR. The corresponding NMR spectra were consistent with the structure of the anticipated product.

Example 15

3(R,S)-Carboxyl-1-ethyl-8-methoxy-7-(piperazin-1-yl)-2,3,4,5-tetrahydro-1H-1-benzazepine-2-one Hydrochloride 3(R,S)-tert-butoxycarbonyl-1-ethyl-8-methoxy-7-[(4-tert-butoxycarbonylpiperazin)-1-yl]-2,3,4,5-tetrahydro-1H-1-benzazepine-2-one (0.50 g, 0.993 mmol) was added portionwise to a solution of 4 M HCl in 1,4-dioxane (6 mL) at 0° C. After stirring the reaction mixture at room temperature for 3 hrs it was cooled at 0° C. Precipitation of the product was effected by adding anhydrous ether (15 mL). The precipitate was collected by filtration, washed with anhydrous ether and dried in vacuum. The desired compound (378 mg, 91%) was obtained as a white powder.

M.P.: 173–176° C. (decomp). $C_{18}H_{25}N_3O_4$ (347.42); MS (FAB) m/e 348 (M+1)$^+$.

This product was also analyzed by $^1$H and $^{13}$C NMR. The corresponding NMR spectra were consistent with the structure of the anticipated product.

Example 16

3(R,S)-tert-Butoxycarbonyl-1-ethyl-8-methoxy-2,3-dihydro-1H-1-benzazepine-2-one

A mixture of 3(R,S)-tert-butoxycarbonyl-1-ethyl-8-methoxy-2,3,4,5-tetrahydro-1H-1-benzazepine-2-one (0.80 g, 2.51 mmol) and N-bromosuccinimide (0.49 g, 2.76 mmol) in chloroform (20 mL) was heated at reflux for 5 hrs. The resulting reaction mixture was washed with saturated aqueous solution of $NaHCO_3$ and water, dried over anhydrous $Na_2SO_4$, filtered and evaporated to dryness. The crude product was purified by flash chromatography on silica gel column eluted with EtOAc/n-hexane (3:7). The fractions containing the fast running component were collected and evaporated to dryness. The desired compound (60 mg, 8%) was obtained as a white crystalline powder.

M.P.:173–174° C. $C_{18}H_{21}NO_4$ (317.38); MS (FAB) m/e 318 (M+1)$^+$.

This product was also analyzed by $^1$H and $^{13}$C NMR. The corresponding NMR spectra were consistent with the structure of the anticipated product.

Alternative Procedure to Prepare 3-tert-Butoxycarbonyl-1-ethyl-8-methoxy-2,3-dihydro-1H-1-benzazepine-2-one A three-necked flask, equipped with reflux condenser, was charged with 3-tert-butoxycarbonyl-1-ethyl-8-methoxy-2,3,4,5-tetrahydro-1H-1-benzazepine-2-one (4.0 g, 12.52 mmol), NBS (2.452 g, 13.76 mmol), N,O-bis(trimethylsilyl)acetamide (1.712 mL, 6.88 mmol), BPO (ca. 20 mg) and carbon tetrachloride (160 mL). The suspension was heated to reflux when another portion (ca. 20 mg) of BPO was added. After being refluxed for 3 hrs, the reaction mixture was diluted with DCM (100 mL), washed with water and dried over $Na_2SO_4$. The reaction was repeated for another 5 times and the combined organic layers were filtered and evaporated. The residue was repeatedly purified by flash chromatograghy on silica column eluted by ethyl acetate/DCM (2.5%) or ethyl acetate/hexane (20%). The crystal residue was further washed with ethyl acetate/hexane (20%) and dried in vacuum, giving the title compound (4.970 g, 21%) as white crystal.

Example 17

7-Bromo-3(R,S)-carboxyl-1-ethyl-8-methoxy-2,3,4,5tetrahydro-1H-1-benzazepine-2-one A solution of 7-bromo-3(R,S)-tert-butoxycarbonyl-1-ethyl-8-methoxy-2,3,4,5-tetrahydro-1H-1-benzazepine-2-one (50 mg, 0.126 mmol) in TFA (1 mL) was stirred at room temperature for 30 min. After this reaction period the reaction mixture was evaporated under reduced pressure to remove the excess of TFA. Thus obtained product was washed with n-hexane and dried in vacuum. The desired compound was obtained as a white powder (43 mg, 100%).

M.P.: 188–189° C. (decomp). $C_{14}H_{16}BrNO_4$ (342.2); MS (FAB, NBA) m/e 343 (M+H)$^+$.

This product was also analyzed by $^1$H and $^{13}$C NMR. The corresponding NMR spectra were consistent with the structure of the anticipated product.

Example 18

3(R,S)-tert-Butoxycarbonyl-1-ethyl-8-methoxy-7-(piperazin-1-yl)-2,3,4,5-tetrahydro-1H-1-benzazepine-2-one An oven-dried flask, charged with 7-bromo-3(R,S)-tert-butoxycarbonyl-1-ethyl-8-methoxy-2,3,4,5-tetrahydro-1H-1-benzazepine-2-one (48 mg, 0.121 mmol), piperazine (12.64 mg, 0.145 mmol), $Pd(OAc)_2$ (2.72 mg, 0.0121 mmol, 10 mole), BINAP (11.65 mg, 0.0182 mmol) was purged with argon for 5 min. After addition of anhydrous toluene (1 mL) through a syringe followed by sodium tert-butoxide (16.78 mg, 0.169 mmol) in one portion, the flask was purged with argon, vigorously stirred and heated at 80° C. for 22 hrs. The course of the reaction was monitored by TLC. The reaction mixture was diluted with DCM (20 mL), percolated through a short column of Celite and evaporated to dryness. Purification of a crude product using preparative silica TLC developed with MeOH/DCM (1:4) provided the desired compound (8.0 mg, 16%) as a white crystalline product.

M.P.: 165° C. (decomp). $C_{22}H_{33}N_3O_4$ (403.52); MS (FAB) m/e 404 (M+1)$^+$.

This product was also analyzed by $^1$H and $^{13}$C NMR. The corresponding NMR spectra were consistent with the structure of the anticipated product.

Example 19

1,4-Di-[(3(R,S)-tert-Butoxycarbonyl-1-ethyl-8-methoxy-2-oxo-2,3,4,5-tetrahydro-1H-1-benzazepine)-7-yl]-piperazine An oven-dried flask, charged with 7-bromo-3(R,S)-tert-butoxycarbonyl-1-ethyl-8-methoxy-2,3,4,5-tetrahydro-1H-1-benzazepine-2-one (300 mg, 0.75 mmol), piperazine (78.6 mg, 0.90 mmol), $Pd(OAc)_2$ (16.8 mg, 0.075 mmol, 10 mol %), BINAP (70.1 mg, 0.1125 mmol) was purged with argon for 5 min and anhydrous toluene (1 mL) was added through a syringe. After addition of $Cs_2CO_3$ (0.342 g, 1.05 mmol) in one portion, the reaction mixture was purged with argon for 3 min, vigorously stirred and heated at 100° C. for 22 hrs. The reaction mixture was diluted with DCM (20 mL), percolated through a short column of Celite and evaporated to dryness. Purification of the crude product by flash chromatography on silica gel column eluted with MeOH/DCM (1:9), provided the desired compound (40 mg, 7%) as a white crystalline product.

M.P.: 146–149° C. $C_{40}H_{56}N_4O_8$ (720.91); MS (FAB) m/e 721 (M+1)$^+$.

This product was also analyzed by $^1$H and $^{13}$C NMR. The corresponding NMR spectra were consistent with the structure of the anticipated product.

Example 20

1,4-Di-[(3(R,S)-Carboxyl-1-ethyl-8-methoxy-2-oxo-2,3,4,5-tetrahydro-1H-1-benzazepine)-7-yl]-piperazine A solution of 1,4-di-[(3(R,S)-tert-butoxycarbonyl-1-ethyl-8-methoxy-2-oxo-2,3,4,5-tetrahydro-1H-1-benzazepine)-7-yl]-piperazine (6 mg, 0.008 mmol) in TFA (1 mL) was stirred at room temperature for 30 min. The reaction mixture was then evaporated to dryness under reduced pressure to remove excess of TFA. After washing the solid product with n-hexane and drying in vacuum the desired compound was obtained as a yellowish powder (5 mg, 75%).

M.P.: 149–152° C. $C_{32}H_4ON_4O_8$ (608.69); MS (FAB, NBA) m/e 609 (M+H)$^+$.

This product was also analyzed by $^1$H and $^{13}$C NMR. The corresponding NMR spectra were consistent with the structure of the anticipated product.

Example 21

7-[(4-tert-Butoxycarbonylpiperazin)-1-yl]-1-ethyl-8-methoxy-2,3,4,5-tetrahydro-1H-1-benzazepine-2-one An oven-dried flask, charged with 7-bromo-1-ethyl-8-methoxy-2,3,4,5-tetrahydro-1H-1-benzazepine-2-one (268 mg, 0.90 mmol), benzyl 1-piperazinecarboxylate (201 mg, 1.08 mmol), Pd(OAc)$_2$ (20.16 mg, 0.09 mmol, 10 mol %), BINAP (84.12 mg, 0.134 mmol) was purged with argon for 5 min. Anhydrous toluene (1.5 mL) was added via syringe. The flask was opened and sodium tert-butoxide (120.0 mg, 1.26 mmol) was added in one portion. After purging with argon for 3 min, the reaction mixture was stirred and heated at 100° C. for 2 hrs. TLC indicated that the starting material has been consumed. The reaction mixture was allowed to cool to ambient temperature, poured into water, extracted with ethyl acetate, dried over $Na_2SO_4$, filtered and evaporated to dryness. Purification of the crude product by flash chromatography on silica gel column eluted with MeOH/DCM (10% of MeOH in DCM) gave the title compound as brownish foam (266 mg, 73%).

M.P.: amorphous compound MS (FAB): calcd for $C_{22}H_{33}N_3O_4$ 403.52; found m/e 404 (M+1)$^+$.

This product was also analyzed by $^1$H and $^{13}$C NMR. The corresponding NMR spectra were consistent with the structure of the anticipated product.

Example 22

1-ethyl-8-methoxy-7-(piperazin-1-yl)-2,3,4,5-tetrahydro-1H-1-benzazepine-2-one hydrochloride 7-[(4-tert-Butoxycarbonyl)-piperazin-1-yl)-1-ethyl-8-methoxy-2,3,4,5-tetrahydro-1H-1-benzazepine-2-one (150 mg, 0.372 mmol) was added portionwise into 4 M solution of HCl in 1,4-dioxane (4 mL) at 0° C. After stirring at room temperature for 3 hrs, the reaction mixture was cooled in ice-water bath and a final product precipitated by addition of anhydrous ether (15 mL). The precipitate was collected by filtration, washed with anhydrous ether and dried in high vacuum. The title compound was obtained as a white foam (135 mg, 96%). MS (FAB): calcd for $C_{17}H_{25}N_3O_2$ 303.41; found m/e 304 (M+1)$^{30}$.

M.P.: amorphous compound; corresponding NMR spectra were consistent with the structure of the anticipated product.

Example 23

1-tert-Butoxycarbonyl-3(R,S)-tert-butoxycarbonyl-8-methoxy-2,3,4,5-tetrahydro-1H-1-benzazepine-2-one 1-tert-Butoxycarbonyl-3(R,S)-tert-butoxycarbonyl-8-methoxy-2,3,4,5-tetrahydro-1H-1-benzazepine-2-one was obtained as a by product in a synthesis of 3-tert-butoxycarbonyl-8-methoxy-2,3,4,5-tetrahydro-1H-1-benzazepine-2-one. The experimental procedure for a preparation of 3-tert-butoxycarbonyl-8-methoxy-2,3,4,5-tetrahydro-1H-1-benzazepine-2-one was repeated with 8-methoxy-2,3,4,5-tetrahydro-1H-1-benzazepine-2-one (10.00 g, 52.26 mmol) as a starting compound. During purification of the reaction mixture by flash chromatography fractions running faster than those containing 3-tert-butoxycarbonyl-8-methoxy-2,3,4,5-tetrahydro-1H-1-benzazepine-2-one were collected and evaporated to dryness. The residue was further purified on silica gel column eluted with ethyl acetate/n-hexane (30% ethyl acetate in n-hexane). Crystallization of the crude product from chloroform/n-hexane (30% chloroform in n-hexane), gave the title compound as a white crystalline product (2.5 g, 12%).

M.P.: 91–92° C. MS (FAB): calcd for $C_{21}H_{29}NO_6$ 391.46; found m/e 392 (M+1)$^+$.

This product was also analyzed by $^1$H and $^{13}$C NMR. The corresponding NMR spectra were consistent with the structure of the anticipated product.

Example 24

7-Bromo-8-methoxy-2,3,4,5-tetrahydro-1H-1-benzazepine-2-one

A suspension of 8-methoxy-2,3,4,5-tetrahydro-1H-1-benzazepine-2-one (100 mg, 0.52 mmol), NBS (103 mg, 0.57 mmol) and BPO (ca. 5 mg) in carbon tetrachloride (1.5 mL) was heated at reflux for 3 hrs. The reaction mixture was allowed to cool to room temperature, diluted with DCM (20 mL), washed with water and dried over $Na_2SO_4$. Filtration and evaporation of the organic layer provided a solid residue, which was washed with n-hexane and dried in high vacuum. The title compound was obtained as a white crystalline product (140 mg, 100%).

M.P.:180–182° C. MS (FAB) calcd for $C_{11}H_{12}BrNO_2$ 270.11; found m/e 271 (M+1)$^+$.

This product was also analyzed by $^1$H and $^{13}$C NMR. The corresponding NMR spectra were consistent with the structure of the anticipated product.

Example 25

3(R,S)-tert-Butoxycarbonyl-1-(3-fluorobenzyl)-8-methoxy-2,3,4,5-tetrahydro-1H-1-benzazepine-2-one A suspension of 3-tert-butoxycarbonyl-8-methoxy-2,3,4,5-tetrahydro-1H-1-benzazepine-2-one (2.0 g, 6.86 mmol), 3-fluorobenzyl bromide (1.68 mL, 13.72 mmol) and $Cs_2CO_3$ (4.48 g, 13.72 mmol) in acetonitrile (20 mL) was stirred at room temperature for 16 hours. The reaction mixture was evaporated to dryness, the residue dissolved in water and extracted with DCM. The organic layer was washed with water, dried over $Na_2SO_4$, filtered and evaporated to dryness. Thus obtained crude product was purified by flash chromatography on silica gel column eluted with ethyl acetate/n-hexane (30% of ethyl acetate in n-hexane). The title compound (2.10 g, 77%) was obtained as a colorless foam.

M.P.: amorphous compound; MS (FAB): calcd for $C_{23}H_{26}FNO_4$ 399.46; found m/e 399 (M)$^+$.

This product was also analyzed by $^1H$ and $^{13}C$ NMR. The corresponding NMR spectra were consistent with the structure of the anticipated product.

Example 26

7-[(4-Benzyloxycarbonyl)-piperazin-1-yl]-3(R,S)-tert-butoxycarbonyl-1-ethyl-8-methoxy-2,3,4,5-tetrahydro-1H-1-benzazepine-2-one An oven-dried flask, charged with 7-bromo-3-tert-butoxycarbonyl-1-ethyl-8-methoxy-2,3,4,5-tetrahydro-1H-1-benzazepine-2-one (240 mg, 0.60 mmol), benzyl 1-piperazinecarboxylate (159 mg, 0.72 mmol), Pd(OAc)$_2$ (14.0 mg, 0.06 mmol, 10 mol %), BINAP (56 mg, 0.09 mmol) was purged with argon for 5 min. Anhydrous toluene (1.5 mL) was added via syringe. The flask was opened and sodium tert-butoxide (80.0 mg, 0.84 mmol) was added in one portion. After purging with argon for 3 min, the reaction mixture was stirred and heated at 100° C. for 2 hrs. Then, the reaction mixture was poured into water, extracted with ethyl acetate and dried over $Na_2SO_4$, filtered and evaporated to dryness. Purification of the crude product by flash chromatography on silica gel column eluted with MeOH/DCM (10% of MeOH in DCM) afforded the title compound as brownish foam (150 mg, 46%).

M.P.: amorphous compound; MS (FAB): calcd for $C_{30}H_{39}N_3O_6$ 537.66; found m/e 538 (M+1)$^+$.

This product was also analyzed by $^1H$ and $^{13}C$ NMR. The corresponding NMR spectra were consistent with the structure of the anticipated product.

Examples 27 and 28

3,7-Dibromo-1-ethyl-3(R,S)-methoxycarbonyl-8-methoxy-2,3,4,5-tetrahydro-1H-1-benzazepine-2-one and 7-Bromo-1-ethyl-3(R,S)-methoxycarbonyl-8-methoxy-2,3,4,5-tetrahydro-1H-1-benzazepine-2-one A mixture of 7-bromo-3(R,S)-tert-butoxycarbonyl-1-ethyl-8-methoxy-2,3,4,5-tetrahydro-1H-1-benzazepine-2-one (100 mg, 0.25 mmol), Br$_2$ (300 mg, 1.88 mmol) and MeOH (5 mL) was stirred at ambient temperature for 24 hours. Then, the reaction mixture was evaporated under reduced pressure to dryness and the residue dried under vacuum at 50° C. for two hours. Thus obtained crude product was dissolved in MeOH (200 mL) and carbon decolorizing was added. After stirring the suspension at ambient temperature for an hour, the reaction mixture was filtrated through a celite pad and the filtrate evaporated to dryness. The residue was dissolved in cold water and extracted with chloroform. The combined extracts were washed with saturated NaHCO$_3$ and brine and dried over MgSO$_4$. TLC (ethyl acetate/:n-hexane, 3:7) of the crude product revealed two new formed products which were separated by flash chromatography with ethyl acetate/n-hexane, 1:1 as an eluent. 45 mg (41%) of 3,7-dibromo-3(R,S)-methoxycarbonyl-1-ethyl-8-methoxy-2,3,4,5-tetrahydro-1H-1-1-benzazepine-2-one was obtained as a white crystalline product. In addition, 36 mg (40%) of 7-bromo-3(R,S)-methoxycarbonyl-1-ethyl-8-methoxy-2,3,4,5-tetrahydro-1H-1-benzazepine-2-one was isolated as a white amorphous product. 3,7-dibromo-1-ethyl-3(R,S)-methoxycarbonyl-8-methoxy-2,3,4,5-tetrahydro-1H-1-benzazepine-2-one:

M.P.: 71–73° C. (decomp). $C_{18}H_{25}BrN_2O_3$ (397.31); MS (FAB) m/e 436 (M+1)$^+$.

This product was also analyzed by $^1H$ NMR. The corresponding NMR spectra were consistent with the structure of the anticipated product. 7-bromo-1-ethyl-3(R,S)-methoxycarbonyl-8-methoxy-2,3,4,5-tetrahydro-1H-1-benzazepine-2-one:

M.P.: amorphous product; $C_{15}H_{17}BrNO_4$ (355.21); MS (FAB) m/e 356 (M+1)$^+$.

This product was also analyzed by $^1H$ NMR. The corresponding NMR spectra were consistent with the structure of the anticipated product.

Example 29

7-bromo-3(R,S)-N-(tert-butyl)aminocarbonyl-1-ethyl-8-methoxy-2,3,4,5-tetrahydro-1H-1-benzazepine-2-one A mixture of 7-bromo-3(R,S)-carboxyl-1-ethyl-8-methoxy-2,3,4,5-tetrahydro-1H-1-benzazepine-2-one (200 mg, 0.58 mmol), 1-[3-dimethylamino]propyl]-3-ethylcarbodiimide hydrochloride (EDCI) (134 mg, 0.70 mmol), and HOBT (108 mg, 0.80 mmol) in anhydrous THF (15 mL) was stirred at room temperature for 30 min. To this solution was added dropwise triethylamine (250 μL) as a neat liquid and the reaction mixture stirred at room temperature for 1.5 hour and subsequently tert-butylamine (46 mg, 0.63 mmol, 100 μL) added as a neat liquid. After the reaction mixture was stirred at ambient temperature for 20 hours, the solvent was evaporated under reduced pressure and the residue was dissolved in ethyl acetate (100 ml), washed with saturated aqueous NaHCO$_3$ and dried over Na$_2$SO$_4$. Flash chromatography of the crude mixture on silica gel column and elution with n-hexane/ethyl acetate, 1:1 afforded the title compound. Trituration of the chromatographed product with n-pentane gave 131 mg (56%) of an off-white crystalline product.

$C_{18}H_{25}BrN_2O_3$ (397.31); MS (EI) m/e 397 (M)$^+$.

This product was also analyzed by $^1H$ and $^{13}C$ NMR. The corresponding NMR spectra were consistent with the structure of the anticipated product.

Example 30

7-Bromo-3(R,S)-tert-butoxycarbonyl-1-(3-fluorobenzyl)-8-methoxy-2,3,4,5-tetrahydro-1H-1-benzazepine-2-one A suspension of 3-tert-butoxycarbonyl-1-(3-fluorobenzyl)-8-methoxy-2,3,4,5-tetrahydro-1H-1-benzazepine-2-one (1.00 g, 2.503 mmol) and NBS (0.49 g, 2.754 mmol) in acetic acid (0.8 mL) and chloroform (8 mL) was heated at reflux for 4 hrs. The reaction mixture was allowed to cool to room temperature, diluted with DCM (30 mL), washed with saturated aqueous sodium bicarbonate solution, dried over Na$_2$SO$_4$. Filtration and evaporation of the organic layer gave a solid residue, which was purified by flash chromatography on silica column eluted with ethyl acetate/n-hexane (25% of ethyl acetate in n-hexane). The title compound was obtained as a white powder (0.400 g, 33%).

M.P.: 146–148° C. MS (FAB): calcd for C$_{23}$H$_{25}$FBrNO$_4$ 478.36; found m/e 478 (M)$^+$.

This product was also analyzed by $^1$H and $^{13}$C NMR. The corresponding NMR spectra were consistent with the structure of the anticipated product.

Example 31

7-[(4-Benzyloxycarbonyl)piperazin-1-yl]-3(R,S)-tert-butoxycarbonyl-1-(3-fluorobenzyl)-8-methoxy-2,3,4,5-tetrahydro-1H-1-benzazepine-2-one An oven-dried flask, charged with 7-bromo-3-tert-butoxycarbonyl-1-(3-fluorobenzyl)-8-methoxy-2,3,4,5-tetrahydro-1H-1-benzazepine-2-one (150 mg, 0.314 mmol), benzyl 1-piperazinecarboxylate (83 mg, 0.376 mmol), Pd(OAc)$_2$ (7.0 mg, 0.03 mmol, 10 mol %), BINAP (28 mg, 0.045 mmol) was purged with argon for 5 min. Anhydrous toluene (1.5 mL) was added via syringe. The flask was opened and sodium tert-butoxide (42.0 mg, 0.44 mmol) was added in one portion as a dry powder. After purging with argon for 3 min, the reaction mixture was stirred and heated at 100° C. for 1.5 hrs. The reaction mixture was cooled to ambient temperature, poured into water, extracted with ethyl acetate, dried over Na$_2$SO$_4$, filtered and evaporated to dryness. Purification of the crude product by flash chromatography on silica gel column eluted with ethyl acetate/n-hexane (50% of ethyl acetate in n-hexane) provided the title compound as brownish foam (60 mg, 32%).

M.P.: amorphous compound MS (FAB): calcd for C$_{35}$H$_{40}$FN$_2$O$_6$ 617.72; found m/e 618 (M+1)$^+$.

This product was also analyzed by $^1$H and $^{13}$C NMR. The corresponding NMR spectra were consistent with the structure of the anticipated product.

Example 32

7-Bromo-3(R,S)-tert-butoxycarbonyl-8-methoxy-2,3,4,5-tetrahydro-1H-1-benzazepine-2-one A suspension of 3-tert-butoxycarbonyl-8-methoxy-2,3,4,5-tetrahydro-1H-1-benzazepine-2-one (1.00 g, 3.43 mmol) and NBS (0.672 g, 3.78 mmol) in acetic acid (0.8 mL) and chloroform (8 mL) was heated at reflux for 3 hrs. Then, the reaction mixture was diluted with DCM (30 mL), washed with water, dried over Na$_2$SO$_4$, filtered and evaporated. The crude residue was purified by flash chromatography on silica column using gradient elution with EtOAc/DCM (from 5% ethyl acetate in DCM to 10% ethyl acetate in DCM). The title compound was obtained as a white powder (0.689 g, 54%).

M.P.: 207–208° C. MS (FAB): calcd for C$_{16}$H$_{20}$BrNO$_4$ 370.24; found m/e 371 (M+1)$^+$.

This product was also analyzed by $^1$H and $^{13}$C NMR. The corresponding NMR spectra were consistent with the structure of the anticipated product.

Example 33

8-Hydroxy-2,3,4,5-tetrahydro-1H-1-benzazepine-2-one

To a solution of 8-methoxy-2,3,4,5-tetrahydro-1H-1-benzazepine-2-one (1.00 g, 5.23 mmol) in DCM (5 mL) was added dropwise 1M solution of BBr$_3$ in DCM (5.23 mL). After stirring at room temperature for 30 min, the reaction mixture was heated at reflux for 5 hrs, allowed to cool to ambient temperature and poured into ice-water. The aqueous layer was extracted with DCM (5×10 mL), dried over Na$_2$SO$_4$, filtered and evaporated. The solid residue was washed with n-hexane and dried in high vacuum. The title compound was obtained as a white powder (705 mg, 76%).

M.P.: 226–227° C.; MS (FAB): calcd for C$_{10}$H$_{11}$NO$_2$ 177.2; found m/e 178 (M+1)$^+$.

This product was also analyzed by $^1$H and $^{13}$C NMR. The corresponding NMR spectra were consistent with the structure of the anticipated product.

Table I contains additional embodiments of the invention according to formula I, wherein a and b are single bonds.

TABLE I

| Ex # | R$^1$ | R$^2$ | R$^3$ | R$^4$ | R$^5$ | Z |
|------|-------|-------|-------|-------|-------|---|
| 34 | —CH$_2$CH$_3$ | —CO$_2$C(CH$_3$)$_3$ | H | 7-phenyl | 8-OCH$_3$ | O |
| 35 | —CH$_2$CH$_3$ | —CO$_2$C(CH$_3$)$_3$ | H | 7-furanyl | 8-OCH$_3$ | O |
| 36 | H | H | H | H | 8-OSi—(CH$_3$)$_2$Bu$^t$ | O |
| 37 | H | —CO$_2$C(CH$_3$)$_3$ | H | H | 8-OH | O |
| 38 | H | H | H | H | 8-NO$_2$ | O |
| 175 | H | H | H | 7-NO$_2$ | 8-OH | O |
| 176 | H | H | —CO$_2$C(CH$_3$)$_3$ | 7-NHC(=S)—NHCO$_2$CH$_2$CH$_3$ | 8-OCH$_3$ | O |

Table II contains additional preferred embodiments of this invention.

TABLE II

Compounds of the formula I

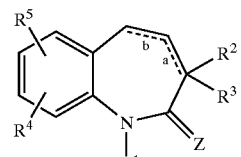

wherein: a and b are a single bond unless noted as a double (dbl) bond in the table below and:

| Ex # | DBL | R¹ | R² | R³ | R⁴ | R⁵ | Z |
|---|---|---|---|---|---|---|---|
| 39 | | 3-F-benzyl | —CH₃ | H | H | 8-F | O |
| 40 | | 3-F-benzyl | —CO₂C(CH₃)₃ | —Br | 7-OCH₃ | H | O |
| 41 | | 3-F-benzyl | —CH₂CH₂CH₃ | —CH₂CH₃ | H | 8-OCH₃ | O |
| 42 | | 3-F-benzyl | —CH₂CH₃ | —CH₃ | 7-(4-butoxy carbonyl-piperazinyl | 8-OCH₃ | O |
| 43 | | 3-F-benzyl | —CH₂CH₃ | —CH₃ | 7-piperazinyl- | 8-OCH₃ | O |
| 44 | | 3-F-Benzyl | —CO₂C(CH₃)₃ | H | H | —NH₂ | S |
| 45 | | 3-F-Benzyl | —CO₂C(CH₃)₃ | H | 7-Br | —NHCH₂CH₃ | S |
| 46 | | tetrahydro-4H-pyran | H | —CH₂CONH₂ | 7-F | H | O |
| 47 | | tetrahydro-4H-pyran | H | —CH₃ | H | 8-OCH₃ | O |
| 48 | | tetrahydro-4H-pyran | H | —CH₃ | H | 8-OCH₃ | S |
| 49 | | —SO₂R | —CH₂CH₃ | H | H | 8-OCH₃ | O |
| 50 | | —CH₂CH₃ | —CO₂C₂H₅ | H | H | 8-NO₂ | O |
| 51 | | —CH₂CH₃ | —COOH | H | H | 8-OH | O |
| 52 | | —CH₂CH₃ | —CO₂C₂H₅ | —CH₂CH₃ | 7-Br | 8-NO₂ | O |
| 53 | | —CH₂CH₃ | —COOH | —CH₂CH₃ | 7-Br | 8-NO₂ | O |
| 54 | | —CH₂CH₃ | H | H | H | 8-OH | O |
| 55 | | —CH₂CH₃ | H | H | 7-Br | 8-OH | O |
| 56 | | —CH₂CH₃ | H | H | 7-(4-CH₃)-piperazinyl- | 8-OH | O |
| 57 | | —CH₂CH₃ | —CO₂C(CH₃)₃ | H | H | 8-NO₂ | O |
| 58 | | —CH₂CH₃ | —CO₂C(CH₃)₃ | H | 7-Br | 8-NO₂ | O |
| 59 | | —CH₂CH₃ | —CO₂C(CH₃)₃ | H | 7-(4-butoxy carbonyl)-piperazinyl- | 8-NO₂ | O |
| 60 | | —CH₂CH₃ | —COOH | H | 7-piperazinyl | 8-OH | O |
| 61 | b | —CH₂CH₃ | —CO₂C(CH₃)₃ | H | —NHC(=O)NH₂ | 8-OH | O |
| 62 | | —CH₂CH₃ | —COOH | H | 7-Br | —NHC(=O)—NHCO₂—CH₂CH₃ | O |
| 63 | | —CH₂CH₃ | —CO₂C(CH₃)₃ | H | 7-piperazinyl--(3-tert-butoxy-carbonyl-1-ethyl-8-methoxy-2-oxo-2,3,4,5-tetrahydro-1H-1-benzazepine)-7-yl-piperazine | 8-OCH₃ | O |
| 64 | | —CH₂CH₃ | —CO₂C(CH₃)₃ | H | | —OSi(CH₃)₂Buᵗ | O |
| 65 | | —CH₂CH₃ | —(CH₂)₂NH₂ | H | -(3carboxyl-1-ethyl-8-methoxy-2-oxo-2,3,4,5-tetrahydro-1H-1-benzaze-pine)-7-yl]-piperazine | 8-OCH₃ | O |
| 66 | | —CH₂CH₃ | —CONH₂ | H | 7-(4-butoxy carbonyl-piperazinyl- | 8-OCH₃ | O |
| 67 | | —CH₂CH₃ | —CONHCH₃ | H | —NO₂ | 8-OCH₃ | O |
| 68 | | —CH₂CH₃ | —CONH-fluoro-phenyl | H | —CN | 8-OCH₃ | O |
| 69 | | —CH₂CH₃ | -Benzyl | 3-Br | —NH₂ | 8-OCH₃ | O |
| 70 | | —CH₂CH₃ | —CH₂—NH-glycine | H | Benzyl- | 8-OCH₃ | O |
| 71 | | —CH₂CH₃ | N-(tert-butyl)amino-carbonyl | H | 7-Br | 8-OCH₃ | O |
| 72 | | —CH₂CH₃ | —CO₂C(CH₃)₃ | —CO₂C(CH₃)₃ | Phenyl- | 8-OCH₃ | O |
| 73 | | —CH₂CH₃ | Benzyl- | H | Furanyl- | 8-OCH₃ | O |
| 74 | b | —CH₂CH₃ | —CO₂C₂H₅ | —Br | H | 8-OCH₃ | O |
| 75 | | —CH₂CH₃ | —CO₂C(CH₃)₃ | —CN | Phenyl- | 8-OCH₃ | S |
| 76 | | —CH₂COCH₃ | —CO₂CH₃ | —F | 7-(4- | 8-OCH₃ | O |

-continued

| Ex # | DBL | R¹ | R² | R³ | R⁴ | R⁵ | Z |
|---|---|---|---|---|---|---|---|
| 77 | | —CH₂COCH₃ | —CO₂C(CH₃)₃ | H | benzyloxy-carbonyl)-piperazinyl- H | 8-piperazinyl- | O |
| 78 | | —CH₂CH₂OH | H | —CH₃ | H | 8-OCH₃ | O |
| 79 | | —CH₂CH₂OH | —CH₃ | —CH₃ | 7-F | 8-OCH₃ | O |
| 80 | | —CH₂CH₂OH | —CH₂CH₃ | H | H | 8-OCH₃ | O |
| 81 | | —CH₂CH₂OH | —CH₂CH₃ | H | 7-NH₂ | H | O |
| 82 | | —CH₂OCH₃ | H | —CH₃ | H | 8-OCH₃ | O |
| 83 | | —CH₂CH₂OH | —CH₂CH₃ | —CH₃ | 7-(4-benzyloxy-carbonyl)-piperazinyl- | 8-OCH₃ | O |
| 84 | | —CH₂—C₅H₄N | H | —CH₃ | H | 8-OCH₃ | S |
| 85 | | —CH₃ | H | —CH₃ | H | 8-OCH₂CH₃ | O |
| 86 | | —CH₃ | —CH₂NH₂ | H | H | 8-OCH₂CH₃ | O |
| 87 | | —CH₃ | —CH₂CH₃ | —CH₂CONH₂ | H | 8-OCH₂CH₃ | O |
| 88 | | —CH₃ | —CH₂CH₂CH₃ | H | H | 8-OCH₂CH₃ | O |
| 89 | | —CH₃ | F-phenyl- | H | H | 8-OCH₂CH₃ | O |
| 90 | | —CH₃ | fluoro-benzyl- | H | H | 8-OCH₂CH₃ | O |
| 91 | | —CH₃ | —CH₂CH₂NHCH₃ | H | H | 8-OCH₂CH₃ | O |
| 92 | | —CH₃ | —(CH₂)₂NHCHO | H | H | 8-OCH₂CH₃ | O |
| 93 | | —CH₃ | —CO₂NH₂ | H | H | 8-OCH₂CH₃ | O |
| 94 | | —CH₃ | —Br | H | H | 8-OCH₂CH₃ | O |
| 95 | | —CH₃ | —CN | H | H | 8-OCH₂CH₃ | O |
| 96 | | —CH₃ | —CH₂CH₃ | H | H | 8-OCH₂CH₃ | O |
| 97 | | —CH₃ | furanyl- | H | H | 8-OCH₂CH₃ | O |
| 98 | | —CH₃ | —COOH | H | piperizinyl- | 8-CH₃ | O |
| 99 | | —CH₃ | —CONH₂ | H | piperidinyl- | 8-CH₃ | O |
| 100 | | —CH₃ | —CH₂CONH₂ | —CH₃ | 7-CH₃ | 8-CH₃ | O |
| 101 | | —CH₃ | —CH₂CONH₂ | —CH₃ | 7-F | 8-CH₃ | O |
| 102 | | —CH₃ | —CH₂NH₂ | —F | 7-OCH₃ | 8-OCH₂CH₃ | O |
| 103 | | —CO₂C(CH₃)₃ | —CO₂C(CH₃)₃ | —H | H | 8-OCH₃ | O |
| 104 | | —CH₂CONH₂ | H | —CH₃ | pyrrolidinyl- | 8-OCH₃ | O |
| 105 | | —CH₂CONH₂ | —CH₃ | H | pyrrolinyl- | 8-OCH₃ | O |
| 106 | | —CH₂CONH₂ | —CH₂CH₃ | H | imadizolidinyl- | 8-OCH₃ | O |
| 107 | | —CH₂CONH₂ | —CH₂CH₂CH₃ | H | pyrazolidinyl- | 8-OCH₃ | O |
| 108 | | —CH₂CONH₂ | phenyl- | H | morpholinyl- | 8-OCH₃ | O |
| 109 | | —CH₂CONH₂ | benzyl- | H | oxazolidinyl- | 8-OCH₃ | O |
| 110 | | —CH₂CONH₂ | CH₃CH₂-fluoro-phenyl- | H | H | 8-OCH₃ | O |
| 111 | | —CH₂CONH₂ | —F | H | H | 8-OCH₃ | O |
| 112 | | —CH₂CONH₂ | —Cl | H | H | 8-OCH₃ | O |
| 113 | | —CH₂CONH₂ | —I | H | H | 8-OCH₃ | O |
| 114 | | —CH₂CONH₂ | —Br | H | H | 8-OCH₃ | O |
| 115 | | —CH₂CONH₂ | —CN | H | H | 8-OCH₃ | O |
| 116 | | —CH₂CONH₂ | CH₃CH₂— | H | H | 8-OCH₃ | O |
| 117 | | —CH₂CONH₂ | fluoro-phenyl- | H | H | 8-OCH₃ | O |
| 118 | | —CH₂CONH₂ | chloro-benzyl- | H | H | 8-OCH₃ | O |
| 119 | | —CH₂CONH₂ | —COCH₃ | H | H | 8-OCH₃ | O |
| 120 | | —CH₂CONH₂ | —COOH | H | H | 8-OCH₃ | O |
| 121 | | —CH₂CONH₂ | —CH₂CONH₂ | H | H | 8-OCH₃ | O |
| 122 | | —CH₂CONH₂ | —CH₂CN | —CH₃ | H | 8-OCH₃ | O |
| 123 | | —CH₂CONH₂ | —CH₃ | H | H | 8-F | O |
| 124 | | —CH₂CONH₂ | —CH₂CH₃ | H | H | 8-Cl | O |
| 125 | | —CH₂CONH₂ | —CH₂CH₂CH₃ | H | H | 8-I | O |
| 126 | | —CH₂CONH₂ | phenyl- | H | H | 8-Br | O |
| 127 | | —CH₂CONH₂ | —CH₂-pyrazole | H | H | 8-piperazinyl- | O |
| 128 | | —CH₂CONH₂ | cyclohexane-CH₂CH₂— | H | H | 8-OCH₂CH₃ | O |
| 129 | | —CH₂CONH₂ | —F | H | H | 8-OH | O |
| 130 | | —CH₂CONH₂ | —Cl | H | H | 8-OCH₃ | O |
| 131 | | —CH₂CONH₂ | —H | H | —NO₂ | 8-OCH₂CH₃ | O |
| 132 | | —CH₂CONH₂ | —Br | —CN | H | 8-OH | O |
| 133 | | —CH₂CONH₂ | —CN | H | phenyl- | 8-OH | O |
| 134 | | —CH₂CONH₂ | —CH₂CH₃ | —CH₂CH₂—CO₂H | H | 8-OH | O |

-continued

| Ex # | DBL | R¹ | R² | R³ | R⁴ | R⁵ | Z |
|---|---|---|---|---|---|---|---|
| 135 | | —CH$_2$CONH$_2$ | fluoro-phenyl- | —CH$_2$CONH-alanine | H | 8-OH | O |
| 136 | | —CH$_2$CONH$_2$ | chloro-phenyl- | H | H | 8-OH | O |
| 137 | | —CH$_2$CONH$_2$ | —N$_3$ | H | H | 8-OH | O |
| 138 | | —CH$_2$CONH$_2$ | H | —N$_3$ | H | 8-OH | O |
| 139 | | —CH$_2$CONH$_2$ | —COOH | H | —CN | 8-OH | O |
| 140 | | —CH$_2$CONH$_2$ | —CONH$_2$ | H | —Br | 8-OH | O |
| 141 | | —CH$_2$CONH$_2$ | —CO$_2$C(CH$_3$)$_3$ | H | 7-piperazinyl- | 8-OCH$_3$ | O |
| 142 | | —CH$_2$CONH$_2$ | N-(tert-butyl)amino carbonyl- | —CO$_2$C—(CH$_3$)$_3$ | 7-piperazinyl- | 8-OCH$_3$ | O |
| 143 | b | —CH$_2$CH$_2$CN | —CH$_2$CH$_3$ | H | H | 8-OCH$_3$ | O |
| 144 | | —CH$_2$O-phenyl | —COOH | H | H | 8-OCH$_2$CH$_3$ | S |
| 145 | | —CH$_2$C(=NH)—NH$_2$ | —CONH$_2$ | H | H | 8-OCH$_2$CH$_3$ | S |
| 146 | | —CH$_2$NH-phenyl | —CO$_2$C(CH$_3$)$_3$ | H | 7-piperazinyl- | 8-OCH$_3$ | S |
| 147 | | —CH$_2$CONH$_2$ | N-(tert-butyl)amino carbonyl | —CO$_2$C—(CH$_3$)$_3$ | 7-piperazinyl- | 8-OCH$_3$ | S |
| 148 | | H | H | H | 8-Br | 7-OCH$_3$ | O |
| 149 | | H | —CO$_2$C$_2$H$_5$ | H | 7-Br | 8-OCH$_3$ | O |
| 150 | | —CH$_2$CN | —CO$_2$C(CH$_3$)$_3$ | H | 7-OCH$_3$ | 8-NO$_2$ | O |
| 151 | | —CH$_2$CN | H | H | 7-Br | 8-OCH$_3$ | O |
| 152 | | —CH$_2$CN | —CO$_2$C(CH$_3$)$_3$ | H | 7-Br | 8-OCH$_3$ | O |
| 153 | | —CH$_2$CH$_3$ | H | H | H | —OH | O |
| 154 | | —CH$_2$CH$_3$ | H | H | —OSi(CH$_3$)$_2$Bu$^t$ | H | O |
| 155 | | H | —CO$_2$C(CH$_3$)$_3$ | H | 7-Cl | 8-OH | O |
| 156 | | —CH$_2$CH$_3$ | H | H | H | 8-NO$_2$ | O |
| 157 | | —OH | H | —CH$_3$ | H | 8-CH$_3$ | O |
| 158 | | —OH | —CH$_3$ | H | H | 8-CH$_3$ | O |
| 159 | | —OH | —CH$_2$CH$_3$ | H | H | 8-CH$_3$ | O |
| 160 | | —OH | —CH$_2$CH$_2$CH$_3$ | H | H | 8-CH$_3$ | O |
| 161 | | —OH | imidazolyl- | H | —OSi(CH$_3$)$_2$Bu$^t$ | 8-CH$_3$ | O |
| 162 | | —OH | benzoyl- | H | H | 8-CH$_3$ | O |
| 163 | | —OH | cyclo-hexane-CH$_2$CH$_2$— | H | H | 8-CH$_3$ | O |
| 164 | | —OH | —F | H | H | 8-CH$_3$ | O |
| 165 | | —OCH$_3$ | —Cl | H | H | 8-CH$_3$ | O |
| 166 | | —OH | —CH$_2$CH$_3$ | H | H | 8-CH$_3$ | O |
| 167 | | —OH | tolyl- | H | H | 8-CH$_3$ | O |
| 168 | | —OH | butyl-ethyl-propyl-phenyl- | H | H | 8-CH$_3$ | O |
| 169 | | —OH | xylyl- | H | H | 8-CH$_3$ | O |
| 170 | | cyclohexyl- | —COOH | H | H | 8-CH$_3$ | O |
| 171 | | —OH | —CH$_2$CONH$_2$ | H | H | 8-CH$_3$ | O |
| 172 | | —OH | —CH$_2$CONH$_2$ | —F | 7-CH$_3$ | 8-CH$_3$ | O |
| 173 | | —SO$_2$R | —F | H | H | 8-OCH$_3$ | O |
| 174 | | —SO$_2$R | —F | H | H | 8-OCH$_3$ | S |

Dosage and Formulation

The compounds of this invention can be administered as treatment for bacterial, viral or fungal infections by any means that produces contact of the active agent with the agent's site of action, the bacteria, virus or fungus in the body of an animal or plant or on the surface of nonliving objects. They can be administered by any conventional means available for use in conjunction with pharmaceuticals, either as individual therapeutic agents or in a combination of therapeutic agents.

They can be administered alone, but generally administered with a pharmaceutical carrier selected on the basis of the chosen route of administration and standard pharmaceutical practice.

They are of course given by forms suitable for each administration route. For example, they are administered in tablets or capsule form, by injection, inhalation, eye lotion, ointment, suppository, etc. administration by injection, infusion, inhalation topically or rectally. Oral administration is preferred. The compounds of the invention are useful for the treatment of infections in hosts, especially mammals, including humans, in particular in humans and domesticated animals (including but not limited to equines, cattle, swine, sheep, poultry, feline, canine and pets in general) and plants. The compounds may be used, for example, for the treatment of infections of, inter alia, the respiratory tract, the urinary/reproductive tract, and soft tissues and blood, especially in humans.

The compounds may be used in combination with one or more therapeutic partners for the treatment of infections. The term "therapeutic partner" or "therapeutic agent" as used herein and in the claims includes but is not limited to antibiotic (for example, tobramycin, cephalosporin), steroids, vaccines, anti-oxidants, non-steroidal anti-inflammatories, antacids, antibodies, interferons, or cytokines.

Examples of therapeutic partners that may be co-administered with the compounds according to the invention include, but are not limited to imipenem, meropenem, biapenem, aztreonam, latamoxef (MOXALACTAM™), and other known beta-lactam antibiotics, benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, sulbenicillin, piperacillin, and other known penicillins. The penicillins may be used in the form of pro-drugs thereof, for example as in vivo hydrolysable esters, for example the acetoxymethyl, pivaloyloxymethyl, alpha-ethoxycarbonyloxyethyl and phthalidyl esters of ampicillin, benzylpenicillin and amoxycillin; as aldehyde or ketone adducts of penicillins containing a 6-alpha-aminoacetamido side chain (for example hetacillin, metampicillin and analogous derivatives of amoxycillin); and as alpha-esters of carbenicillin and ticarcillin, for example the phenyl and indanyl alpha-esters. Cephalosporins that may be therapeutic partners with the compounds according to the invention include, but are not limited to, cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefinetazole, cefotaxime, ceftriaxone, and other known cephalosporins. All of therapeutic partners may be used in the form of pro-drugs thereof.

When the compounds of the invention are co-administered with a therapeutic partner, the ratio of the amount of the compound according to the invention to the amount of the therapeutic partner may vary within a wide range. The said ratio may, for example, be from 100:1 to 1:100; more particularly, it may, for example, be from 2:1 to 1:30. The amount of the therapeutic will normally be approximately similar to the amount in which it is conventionally used per se, for example from about 50 mg, advantageously from about 62.5 mg, to about 3000 mg per unit dose, more usually about 125, 250, 500 or 1000 mg per unit dose.

It is generally advantageous to use a compound according to the invention in admixture or conjunction with a therapeutic partner that can result in a synergistic effect The compound of the invention can be administered separately or in the form of a single composition containing both active ingredients. The compound of the invention and the therapeutic partner may be administered simultaneously or sequentially. Examples of simultaneous administration include where two or more compounds, compositions, or vaccines which may be the same or different, are administered in the same or different formulation or are administered separately, e.g. in a different or the same formulation but within a short time (such as minutes or hours) of each other. Examples of sequential administration include where two or more compounds, compositions or vaccines which may be the same or different are not administered together within a short time of each other, but may be administered separately at intervals of for example days, weeks, months or years.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent. dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, bismuth,and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day, preferably from 5 to 500 mg. Each unit dose may be, for example, 5, 10, 25, 50, 100, 125, 150, 200 or 250 mg of a compound according to the invention. If desired, the effective daily dose of the active compound may be administered as two, three, four, five, six or more sub-doses administered separately at appropriate intervals throughout the day, optionally, in unit dosage forms For use in agricultural applications, the compound or compositions of the invention is suspended in an agriculturally acceptable diluent, including but not limited to water or a fertilizer solution. To assure better adhesion of the liquid for example, in the case when the suspension is applied to the plant surface, glycerin can be added to the final diluted liquid formulation. The compounds or compositions of the invention is mixed as a dry ingredients with an inert agriculturally acceptable particulate dry carrier or diluent which provides a fine powdery formulation. The agriculturally acceptable diluent is one that serves as a carrier for the low concentrations of compounds or compositions of the invention. Preferably the dry diluent is one which readily suspends in suitable diluents for administration to plants, such as water.

The formulation is applied to the plant by any of a variety of art-recognized means. For example, the formulation can be applied to the plant surface by spraying. Alternatively, the solution can be introduced injectably into a plant, for example, with a syringe, applied as a solid fertilized-like preparation for absorption by the roots at the base of a plant or a solution can be distributed at the base of a plant for root absorption. The formulation can be applied as soon as symptoms appear or prophylactically before symptoms appear. Application can be repeated.

Utility

The present invention is the result of the unexpected discovery that substituted 1-benzazepines and analogs thereof defined by formulae I inhibit growth and/ or the life of bacteria. Accordingly, pharmaceutical compositions containing the compounds of structural formula I inhibit bacteria and are useful as pharmaceutical agents for animals, especially mammals, including humans, for the treatment of bacterial diseases. In one embodiment of the invention bacterial diseases those caused by, but are not limited to, Streptococcus spp., Staphylococcus spp., Clostridium spp., Borrelia spp., Haemophilus spp., Pseudomonas spp., Neisseria spp., Coxiella spp., Shigella spp., Campylobacter spp., Enterococcae spp., *E. coli* spp., Helicobacter spp., Klebsiella spp., Moraxella spp., Chlamydia spp., Mycobacteria spp., other nosocomial infections, respiratory infections and enteric infections. More preferred are infections caused by methicillin resistant *Staphylococcus aureus* ("MRSA"), *Neisseria gonorrhoeae, Mycobacteria tuberculosis*, vancomycin resistant Enterococcae ("VRE"), *Helicobacter pylori, Chlamydia pneumoniae, Chylamydia trachomatis* and *Camplylobacter jejuni*.

The present invention is also useful in a method directed to treating infections in a host in need of such treatment, which method comprises administering a non-toxic (to the host) therapeutically effective amount of compounds represented by general Formula I. In one embodiment, the infected hosts are animals, preferably mammals, most preferably human, especially immunologically compromised individuals. In another embodiment, the infected host is a plant.

Optionally, nonliving material such as but not limited to soil, surfaces, etc., may be usefully treated with the instant compounds to kill bacteria.

The present invention is also useful in a method of treating cancer, central nervous system, cardiovascular, inflammatory, or autoimmune disease in a host in need of such treatment, which method comprises administering a non-toxic (to the host) therapeutically effective amount of compounds represented by general Formula I. In one embodiment, the infected hosts are animals, preferably mammals, most preferably human.

The antibiotic preparation can also be used in a wide variety of agriculturally beneficial species such as tobacco, vegetables including cucumber, the Cruciferae, pea and corn, beans such as soy beans, grains including cotton, rice, alfalfa, oat and other cereals, fruits, including apple, pear, peach, plum, tomato, banana, prune and citrus fruits, tubers and bulbs including potatoes and onions, nuts including walnut, grasses including sugar cane and the like.

The antibiotic preparation also is beneficial in the treatment of nursery plants and ornamental plants such as flowers, including chrysanthemum, begonia, gladiolus, geranium, carnations and gardenias.

The compositions of the instant invention also find use in the treatment of shade trees, forest trees, annual field crops and biannual field crops.

Other plant species in which the compositions of the invention can be used are Espinas, Cotoneaster, Phyrachanthas, Stranvaesis, Fraxinus, Pyrus, Malus, Capsicum, Cydonia, Crataegus and Soreus.

Besides their use as medicaments in human, veterinary or plant therapy, the compounds of the invention can also be used as animal growth promoters. For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration. Alternatively, an intermediate concentrate or feed supplement containing the active ingredient can be blended into the feed. The way in which such feed premixes and complete rations can be prepared and administered are described in reference books (such as such as "Applied Animal Nutrition", W. H. Freedman and CO., S. Francisco, USA, 1969 or "Livestock Feeds and Feeding" O and B books, Corvallis, Oreg., USA, 1977).

Antibacterial activity can be determined by several standard methods well known by those skilled in the art, including disc diffusions methods, broth dilution minimal inhibitory concentration (MIC) methods, etc., including the detailed method outlined below.

Anti-fungal activity can be determined by several standard methods well known by those skilled in the art (see for instance, U.S. Pat. No. 5,885,782), including disc diffusion methods, broth dilution minimal inhibitory concentration (MIC) methods and microplate growth assay.

MIC, Broth Dilution Method

A. Starting Culture

Cultures of bacteria are initially brought up from the freezer stocks onto chocolate agar plates by streaking a loop-full, then incubated for 18 hours at 35–37° C. in a 5% CO2 incubator.

B. First Subculture

Five to 10 colonies are picked from the chocolate agar plate for subculture to Brain-Heart Infusion (BHI) broth or Mueller Hinton broth or BHI containing 4% serum and incubated as described.

C. Final Culture

Evaluate the optical density of the organisms with and without the test compound. The optical density of the organisms in the presence of an active compound will be less than the optical density of the same organism untreated. The activity of the compounds is described as either negative or the lowest concentration inhibiting growth. The results are depicted in Table III, where +/− represents the least activity and ++++ represents the greatest activity.

TABLE III

| Value of Antibacterial activity: | |
|---|---|
| Example # | Antibacterial Activity |
| 2 | ++ |
| 3 | ++ |
| 4 | +++ |
| 5 | +++ |
| 6 | +++ |
| 7 | + |
| 8 | ++ |
| 9 | +++ |

TABLE III-continued

| Value of Antibacterial activity: | |
|---|---|
| Example # | Antibacterial Activity |
| 10 | +/− |
| 11 | + |
| 12 | + |
| 13 | ++ |
| 14 | + |
| 15 | − |
| 16 | ++++ |
| 17 | +/− |
| 18 | + |
| 20 | + |
| 21 | +++ |
| 22 | − |
| 23 | ++ |
| 24 | + |
| 25 | +++ |
| 26 | +++ |
| 27 | ++ |
| 28 | ++ |
| 29 | − |
| 30 | ++++ |
| 31 | ++++ |
| 32 | ++++ |
| 33 | ++++ |
| 34 | +++ |
| 35 | +++ |
| 36 | ++++ |
| 37 | ++ |
| 38 | + |
| 175 | +++ |
| 176 | ++++ |

Optionally, nonliving material such as but not limited to soil, porous and non-porous surfaces, etc., may be usefully treated with the instant compounds to kill bacteria and sanitize.

EXAMPLES FOR ANTIBIOTIC EVALUATION

Example #177

Colonization Model

The Helicobacter gastric colonization model, using methods generally known to those skilled in the art, is employed to evaluate the antibiotic activity against H. pylori or H. felis in vivo. For example, groups of female Balb/C mice (~6 weeks of age) are colonized, then treated with test compound (for example, one week later). Following a period of time, half of the stomach from mice are scraped and plated onto bacterial culture medium, for instance BHI agar containing antibiotics and horse serum. The plates are incubated and colonies counted to determine whether any bacteria can be recovered in the gastrointestinal tract after treatment. Additionally, urease enzymatic assay, using methods generally known to those skilled in the art, is used to determine whether urease activity from Helicobacter is present. The absence of or reduction of bacteria on the culture plate or urease activity from treated mice, compared to that from non-treated mice, indicates the test substance is effective as an antibiotic against H. pylori or H. felis.

Example #178

Sepsis Model

The sepsis model, using methods generally known by those skilled in the art, is used to evaluate the prophylactic antibiotic efficacy of test compounds against a number of bacteria. Basic methods include, for example, challenging mice intraperitoneally with a lethal amount of one or more bacteria, for example *Staphylococcus aureus*, and 7% mucin. Approximately 1 hr after challenge, the mice are treated by any route of administration, for example, subcutaneously, orally or intraperitoneally, with various concentrations of test compound. Vancomycin or another antibiotic is administered to a group of mice as the positive control and the placebo group of mice is administered the vehicle alone. Mortality is monitored for 96 hr. A reduction of the comparative mortalities or an increase in survival time in the various experimental groups provides evidence of efficacy of the test compound.

Example #179

Wound Infection Model

The wound healing model, using methods generally known by those skilled in the art, is used to measure the efficacy of topically applied compounds against any bacteria, for example, *Staphylococcus aureus*. Basic methods include, for example, inserting a suture impregnated with *S. aureus* subcutaneously on the shaved backs of mice. An incision is made along the cord. After 24 hrs, topical therapy with the test compound, placebo ointment or neomycin-polymyxin-B-bacitracin topical ointment (as control) (twice daily) is initiated. Ninety-six hours post-infection, the wound is sampled for microbial burden.

Alternatively, the backs of mice or rabbits are shaved. Gently scraping the skin, a superficial wound is created. About 10(6) cfu/20 ul of any bacteria, for example, *S aureus*, is applied to the wound. The latter is occluded with a sterile plastic film and secured with an adhesive tape. Topical therapy is employed using the above-mentioned treatment regimen. The wound is swabbed to determine the microbial load. A reduction is bacterial load in the wound is evidence that the compound is efficacious.

Example #180

Shigella Wasting Model

Using methods well known to those skilled in the art, the Shigella sublethal wasting model is used to evaluate the antibiotic activity against *Shigella flexneri* or *Shigella sonnei*. For example, groups of mice are challenged intranasally with a sublethal wasting dose (~$10^5$ cfu) of either live *Shigella flexneri* or *Shigella sonnei*. Immediately before and at 1, 2, 5 and 7 days following challenge animals are weighed and the mean group weight determined. Approximately 1 hour after challenge, the mice are treated by any route of administration, for example, subcutaneously, orally or intravenously, with various concentrations of test compound. A suitable antibiotic is administered to a group of mice as the positive control and the placebo group of mice is administered vehicle alone. Antibiotic activity is measured by a reduction of weight loss.

Example #181

*Campylobacter jejuni* Lethality Model

Using methods well known to those skilled in the art, the *C. jejuni* mortality model is used to evaluate the antibiotic activity against *Campylobacter jejuni*. For example, groups of mice are challenged with a single lethal dose of live *C. jejuni* (~$10^8$ cfu) mixed with iron dextran in endotoxin free PBS delivered intraperitoneally. Approximately 1 hour after challenge, the animals are treated by any route of administration, for example, subcutaneously, orally or intraperitoneally, with various concentrations of test compound. A suitable antibiotic is administered to a group of animals as the positive control and the placebo group of animals is administered vehicle alone. Antibiotic activity is measured by a reduction in mortality.

Example #182

*Campylobacter jejuni* Fecal Shedding Model

Using methods well known to those skilled in the art, the *C. jejuni* fecal shedding model is used to evaluate the antibiotic activity against *Campylobacter jejuni*. For example, BALB/c mice are challenged nasally or orally with $10^8$ *C. jejuni*. Approximately 1 hour after challenge, the mice are treated by any route of administration, for example, subcutaneously, orally or intraperitoneally, with various concentrations of test compound. A suitable antibiotic is administered to a group of mice as the positive control and the placebo group of mice is administered vehicle alone. The duration of fecal shedding is determined by monitoring over a 9 day period. Antibiotic activity is measured by a reduction in numbers of bacteria shed.

Example #183

*Chlamydia pneumoniae* Lung Model

Using methods well known to those skilled in the art, the *Chlamydia pneumoniae* lung model is used to evaluate the antibiotic activity against *Chlamydia pneumoniae*. For example, BALB/c are inoculated intranasally with approximately $5 \times 10^5$ IFU of *C. pneumoniae*, strain AR39 in 100 $\mu$l of SPG buffer. Approximately 1 hour after challenge, the mice are treated by any route of administration, for example, subcutaneously, orally or intravenously, with various concentrations of test compound. A suitable antibiotic is administered to a group of mice as the positive control and the placebo group of mice is administered vehicle alone.

Lungs are taken from mice at days 5 and 9 post-challenge and immediately homogenized in SPG buffer (7.5% sucrose, 5 mM glutamate, 12.5 mM phosphate pH 7.5). The homogenate is stored frozen at −70° C. until assay. Dilutions of the homogenate are assayed for the presence of infectious Chlamydia by inoculation onto monolayers of susceptible cells (for example HL cells). The inoculum is centrifuged onto the cells and the cells are incubated for three days at 35° C. in the presence of 1 $\mu$g/ml cycloheximide. After incubation the monolayers are fixed with formalin and methanol then immunoperoxidase stained for the presence of Chlamydial inclusions using convalescent sera from rabbits infected with *C. pneumoniae* and metal-enhanced DAB as a peroxidase substrate. Antibiotic activity is measured by a reduction in numbers of Chlamydia.

Example #184

*Chlamydia trachomatis* Infertility Model

Using methods well known to those skilled in the art, the *Chlamydia trachomatis* infertility model is used to evaluate the antibiotic activity against *Chlamydia trachomatis*. Female C3HeOuJ mice are administered a single intraperitoneal dose of progesterone (2.5 mg in pyrogen-free PBS, Depo-Provera, Upjohn) to stabilize the uterine epithelium. One week later, animals are infected by bilateral intraoviduct inoculation with approximately $5 \times 10^5$ inclusion forming units (IFU) of *C. trachomatis* (including but not limited to serovar F, strain NI1) in 100 μl of sucrose phosphate glutamate buffer (SPG). At the appropriate time (for example, approximately 1 hour or 1 week after challenge), the mice are treated by any route of administration, for example, subcutaneously, orally or intravenously, with various concentrations of test compound. A suitable antibiotic is administered to a group of mice as the positive control and the placebo group of mice is administered vehicle alone. At week 3, females from each group are caged with 8–10 week old male C3H mice for a 2 month breeding period to assess fertility (1 male for every 2 females per cage with weekly rotation of the males within each group, animals from different experimental groups were not mixed). Palpation and periodic weighing are used to determine when animals in each pair become pregnant. The parameters used to estimate group fertility are: F, the number of mice which littered at least once during the mating period divided by the total number of mice in that study group; M, the number of newborn mice (born dead or alive) divided by the number of litters produced in that group during the mating period; and N, the number of newborn mice (born dead or alive) divided by the total number of mice in that group. Antibiotic activity is measured by an increase in fertility.

Example #185

*Neisseria gonorrhoeae* Lethality Model

Using methods well known to those skilled in the art, the *N. gonorrhoeae* mortality model is used to evaluate the antibiotic activity against *Neisseria gonorrhoeae*. For example, groups of mice are challenged with a single lethal dose of live *N. gonorrhoeae* (~$10^8$ cfu) and 7% mucin in endotoxin free PBS delivered intraperitoneally. Approximately 1 hour after challenge, the animals are treated by any route of administration, for example, subcutaneously, orally or intraperitoneally, with various concentrations of test compound. A suitable antibiotic is administered to a group of animals as the positive control and the placebo group of animals is administered vehicle alone. Antibiotic activity is measured by a reduction in mortality.

Example #186

*Neisseria gonorrhoeae* Vaginal Challenge Model

Using methods well known to those skilled in the art, the *N. gonorrhoeae* vaginal infection model is used to evaluate the antibiotic activity against *Neisseria gonorrhoeae*. For example, groups of mice are vaginally challenged with a dose of live *N. gonorrhoeae* in endotoxin free PBS. Approximately 1 hour after challenge, the animals are treated by any route of administration, for example, subcutaneously, orally or intraperitoneally, with various concentrations of test compound. A suitable antibiotic is administered to a group of animals as the positive control and the placebo group of animals is administered vehicle alone. Vaginal clearance rates are determined for each group by daily sampling (swab) and cultivation of vaginal secretions. Antibiotic activity is measured by a reduction in the number of *N. gonorrhoeae*.

While the preferred embodiments of the invention have been illustrated and described, it will be appreciated that various changes can be made therein without departing from the spirit and scope of the invention.

What is claimed is:
1. A compound of formula (I):

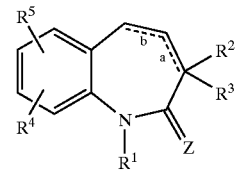

wherein:
$R^1$ is H, substituted or unsubstituted, straight chain, branched or cyclic, alkyl, alkenyl, or alkynyl, substituted or unsubstituted —Ar or —$(CH_2)_n$Ar, —$(CH_2)_m$C(=O)R, —$(CH_2)_n$CN, —$(CH_2)_m$C(=Q)OR, —C(=O)N(R)$_2$, —OR, —SO$_2$R, —C(=O)N(H)(NHR), —CH$_2$(OR), —$(CH_2)_n$(OAr), —$(CH_2)_m$C(=NH)NH$_2$, or —$(CH_2)_n$NHAr, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino;

$R^2$ and $R^3$ are independently H, —CN, —$(CH_2)_m$C(=O)NHOR, —$(CH_2)_m$C(=O)OR, —$(CH_2)_m$C(=O)NH(Aa), —$(CH_2)_m$C(=O)N(R)$_2$, or —$(CH_2)_n$C(=O)NH(Aa), with the proviso that $R^2$ and $R^3$ cannot both be H;

$R^4$ and $R^5$ are independently H, halogen, —NO$_2$, —CN, substituted or unsubstituted, straight chain, branched or cyclic, alkyl, alkenyl, or alkynyl, substituted or unsubstituted —Ar or —$(CH_2)_n$Ar, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino; substituted or unsubstituted primary amine or secondary amine, —NHC(=O)R, —QR, —NHC(=Q)NHC(=O)OR, —NHC(=Q)NHR, —OC(=O)N(R)$_2$, —C(=O)OR, or —OSi(R)$_3$, with the proviso that $R^4$ and $R^5$ cannot both be H;

R is H, a substituted or unsubstituted straight chain, branched or cyclic lower alkyl, lower alkenyl or lower alkynyl, or a substituted or unsubstituted Ar or —$(CH_2)_n$Ar, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino;

Q is O or S;
Z is O or S;
a is a single bond and b is only a double bond;
m is 0, 1 or 2;
n is 1, 2 or 3;
Ar is aryl, arylalkyl, heterocycle, heterocyclic group, heterocyclic, heterocyclyl, or heteroaryl, wherein heterocycle, heterocyclic group, heterocyclic or heterocyclyl is any mono-, bi- or tricyclic saturated, unsaturated or aromatic ring where at least one ring is a 5-, 6- or 7-membered hydrocarbon ring containing from one to four heteroatoms selected from nitrogen, oxygen and sulfur and wherein heteroaryl is any mono-, bi- or tricyclic aromatic rings having the number of ring atoms designated where at least one ring is a 5-, 6- or 7-membered hydrocarbon ring containing from one to four heteroatoms selected from nitrogen, oxygen and sulfur;

Aa is a natural or synthetic amino acid;
or pharmaceutically acceptable acid addition salts, or base addition salts thereof.

2. A compound of formula (I):

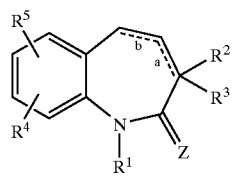

wherein:
- $R^1$ is H, substituted or unsubstituted, straight chain, branched or cyclic, alkyl, alkenyl, or alkynyl, substituted or unsubstituted —Ar or —$(CH_2)_n$Ar, —$(CH_2)_m$C(=O)R, —$(CH_2)_n$CN, —$(CH_2)_m$C(=Q)OR, —C(=O)N(R)$_2$, —OR, —SO$_2$R, —C(=O)N(H)(NHR), —CH$_2$(OR), —$(CH_2)_n$(OAr), —$(CH_2)_m$C(=NH)NH$_2$, or —$(CH_2)_n$NHAr, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino;
- $R^2$ and $R^3$ are independently H, —CN, —$(CH_2)_m$C(=O)NHOR, —$(CH_2)_m$C(=O)OR, —$(CH_2)_m$C(=O)NH(Aa), —$(CH_2)_m$C(=O)N(R)$_2$, or —$(CH_2)_n$C(=O)NH(Aa), with the proviso that $R^2$ and $R^3$ cannot both be H;
- $R^4$ and $R^5$ are independently substituted straight chain, branched or cyclic alkyl wherein the substituents on the alkyl are F, Cl, Br, I, nitro, amino, cyano, hydroxy or carboxyl, substituted or unsubstituted, straight chain, branched or cyclic, alkenyl, or alkynyl, substituted or unsubstituted —Ar or —$(CH_2)_n$Ar, —NHR, —N(R)$_2$, —NHC(=O)R, —QR, —NHC(=Q)NHC(=O)OR, —NHC(=Q)NHR, —OC(=O)N(R)$_2$, —C(=O)OR, or —OSi(R)$_3$;
- R is a substituted straight chain, branched or cyclic lower alkyl, wherein the substituents on the alkyl are F, Cl, Br, I, nitro, amino, cyano, hydroxy or carboxyl, substituted or unsubstituted straight chain, branched or cyclic lower alkenyl or lower alkynyl, or a substituted or unsubstituted Ar or —$(CH_2)_n$Ar;
- Q is O or S;
- Z is O or S;
- a and b are a single bond;
- m is 0, 1 or 2;
- n is 1, 2 or 3;
- Ar is aryl, arylalkyl, heterocycle, heterocyclic group, heterocyclic, heterocyclyl, or heteroaryl, wherein heterocycle, heterocyclic group, heterocyclic or heterocyclyl is any mono-, bi- or tricyclic saturated, unsaturated or aromatic ring where at least one ring is a 5-, 6- or 7-membered hydrocarbon ring containing from one to four heteroatoms selected from nitrogen, oxygen and sulfur and wherein heteroaryl is any mono-, bi- or tricyclic aromatic rings having the number of ring atoms designated where at least one ring is a 5-, 6- or 7-membered hydrocarbon ring containing from one to four heteroatoms selected from nitrogen, oxygen and sulfur;

Aa is a natural or synthetic amino acid;
or pharmaceutically acceptable acid addition salts, or base addition salts thereof.

3. The compound of claim 1 or claim 2, wherein Z is O.

4. The compound of claim 3, having the Formulae:

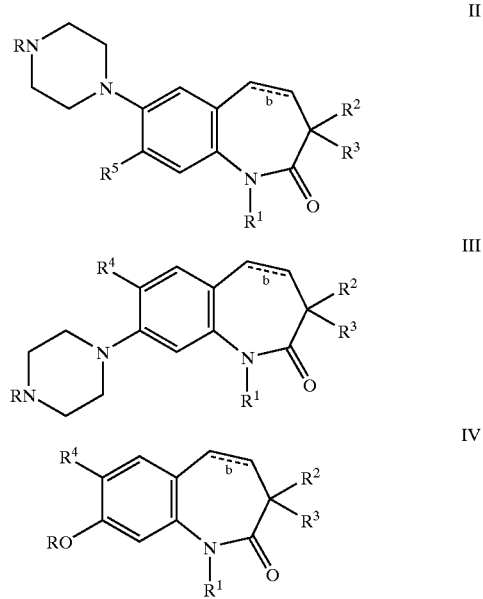

5. The compound of claim 1, wherein $R^1$ is alkyl or alkylfluorobenzyl; $R^2$ or $R^3$ is H, —C(=O)OR, —C(=O)NHAa and —C(=O)N(R)$_2$ with the proviso that $R^2$ and $R^3$ cannot both be H, $R^4$ and $R^5$ are independently H, halogen, alkoxy, —OR, substituted piperazinyl or piperizinyl and a is a single bond and b is only a double bond.

6. The compound of claim 1, wherein $R^2$ and $R^3$ are independently H, —$(CH_2)_m$C(=O)OR, or —$(CH_2)_m$C(=O)NH(Aa), with the proviso that $R^2$ and $R^3$ cannot both be H; and m is 0.

7. The compound of claim 1, wherein $R^1$ is H, $R^2$ and $R^3$ are independently H, —$(CH_2)_m$C(=O)OR, —$(CH_2)_m$C(=O)N(R)$_2$ or —$(CH_2)_m$C(=O)NH(Aa) with the proviso that $R^2$ and $R^3$ cannot both be H; $R^4$ and $R^5$ are independently H, halogen, —NO$_2$, —CN, substituted or unsubstituted, straight chain, branched or cyclic, alkyl, alkenyl, or alkynyl, substituted or unsubstitited —Ar or —$(CH_2)_n$Ar, substituted or unsubstituted primary amine or secondary amine, or —QR, with the proviso that $R^4$ and $R^5$ cannot both be H; m is 0; Q is O; and Z is O.

8. A pharmaceutical antibacterial composition comprising a pharmaceutically effective antibacterial amount of the compound of claim 1 or claim 2 and a pharmaceutically acceptable carrier.

9. The pharmaceutical composition of claim 8, wherein said composition is in a sustained release form.

10. The pharmaceutical composition of claim 8, wherein said carrier is one or more of lactose, starch, cellulose derivatives, magnesium stearate, stearic acid, water, oil, saline, aqueous dextrose, propylene glycol, polyethylene glycols, and water soluble salt.

11. The pharmaceutical composition of claim 8, wherein said composition further comprises one or more of a stabilizer, colorant, taste modifier and adjuvant.

12. The pharmaceutical composition of claim 8, wherein said composition contains about 0.01 to about 100 mg of the compound of claim 1 or claim 2 as an active ingredient per a dose of said composition.

13. The pharmaceutical composition of claim 8, wherein said composition contains about 0.5 to 95% by weight of the compound based on a total weight of the composition.

14. The pharmaceutical composition of claim 8, wherein a daily dosage of said compound is 0.0001 to 1000 mg per kilogram of body weight.

15. The pharmaceutical composition of claim 8, wherein said composition further comprises one or more additional therapeutic agents.

16. The pharmaceutical composition of claim 8, wherein said composition is in a form of an oral dosage selected from the group consisting of capsules, tablets, powders, gel tablets, elixirs, syrups and suspensions.

17. The pharmaceutical composition of claim 8, wherein said composition is in a form of a topical or parenteral solution.

18. The pharmaceutical composition of claim 17, wherein said solution comprises water, oil, saline, aqueous dextrose, sugar solution, or glycols.

19. The pharmaceutical composition of claim 17, wherein said solution comprises a water soluble salt of the compound.

20. The pharmaceutical composition of claim 19, wherein said composition further comprises one or more of a stabilizing agent, a buffer, and a preservative.

21. The pharmaceutical composition of claim 20, wherein said stabilizing agent comprises one or more of sodium bisulfite, sodium sulfite, ascorbic acid, citric acid, citric acid salts, and sodium EDTA.

22. The pharmaceutical composition of claim 8, wherein said composition inhibits the growth of bacteria selected from the group consisting of Streptococcus spp., Staphylococcus spp., Clostridium spp., Borrelia spp., Haemophilus spp., Pseudomonas spp., Neisseria spp., Coxiella spp., Shigella spp., Campylobacter spp., Enterococcae spp., *E. coli* spp., Helicobacter spp., Klebsiella spp., Moraxella sp., Chlamydia sp., Mycobacteria spp., and vancomycin resistant Enterococcae.

23. A sanitizing composition comprising the compound of claim 1 or claim 2.

24. A method for the treatment of bacterial infections which comprises administering to a host in need of such treatment a therapeutically effective amount of a compound of Formula I, as defined in claim 1 or claim 2.

25. A method of killing bacteria on an inert surface or sanitizing said surface comprising applying a compound of Formula I, as defined in claim 1 or claim 2.

26. The compound of claim 2 wherein $R^4$ and $R^5$ are independently piperazinyl or substituted piperazinyl.

27. The compound of claim 2, wherein $R^1$ is H; $R^2$ and $R^3$ are independently H, —$(CH_2)_mC(=O)OR$, —$(CH_2)_mC(=O)N(R)_2$ or —$(CH_2)_mC(=O)NH(Aa)$ with the proviso that $R^2$ and $R^3$ cannot both be H.

28. A method for the treatment of bacterial infections which comprises administering to a host in need of such treatment a therapeutically effective amount of a compound of Formula I:

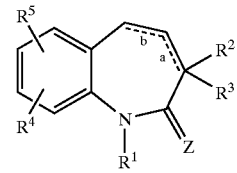

wherein:

$R^1$ is H, substituted or unsubstituted, straight chain, branched or cyclic, alkyl, alkenyl, or alkynyl, substituted or unsubstituted —Ar or —$(CH_2)_nAr$, —$(CH_2)_mC(=O)R$, —$(CH_2)_nCN$ —$(CH_2)_mC(=Q)OR$, —$C(=O)N(R)_2$, —OR, —$SO_2R$, —$(CH_2)_n(OAr)$, —$(CH_2)_mC(=NH)NH_2$, —$(CH_2)_nNHAr$, —$C(=O)N(H)(NHR)$, or $CH_2(OR)$, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino;

$R^2$ and $R^3$ are independently H, halogen, —$N_3$, —CN, substituted or unsubstituted, straight chain, branched or cyclic, alkyl, alkenyl, or alkynyl, substituted or unsubstituted —Ar or —$(CH_2)_nAr$, —$(CH_2)_mN(R)_2$, —$(CH_2)_mNH(Aa)$, —$(CH_2)_mNC(=O)R$, —$(CH_2)_mC(=O)ONHOR$, —$(CH_2)_mC(=O)OR$, —$(CH_2)_mC(=O)NH(Aa)$, —$(CH_2)_mC(=O)N(R)_2$, or —$(CH_2)_nC(=O)NH(Aa)$;

$R^4$ and $R^5$ are independently H, halogen, —$NO_2$, —CN, substituted or unsubstituted, straight chain, branched or cyclic, alkyl, alkenyl, or alkynyl, substituted or unsubstituted —Ar or —$(CH_2)_nAr$, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino; substituted or unsubstituted primary amine or secondary amine, —$NHC(=O)R$, —QR, —$OC(=O)N(R)_2$, $NHC(=Q)NHC(=O)OR$, —$NHC(=Q)NHR$, —$C(=O)OR$, or —$OSi(R)_3$;

R is H, a substituted or unsubstituted straight chain, branched or cyclic lower alkyl, lower alkenyl or lower alkynyl, or a substituted or unsubstituted Ar or $(CH_2)_nAr$, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino;

Q is O or S;

Z is O or S;

a and b are a single or double bond, and when a is a double bond, only $R^2$ or $R^3$ are present;

m is 0, 1 or 2;

n is 1, 2 or 3;

Ar is aryl, arylalkyl, heterocycle, heterocyclic group, heterocyclic, heterocyclyl, or heteroaryl, wherein heterocycle, heterocyclic group, heterocyclic or heterocyclyl is any mono-, bi- or tricyclic saturated, unsaturated or aromatic ring where at least one ring is a 5-, 6- or 7-membered hydrocarbon ring containing from one to four heteroatoms selected from nitrogen, oxygen and sulfur and wherein heteroaryl is any mono-, bi- or tricyclic aromatic rings having the number of ring atoms designated where at least one ring is a 5-, 6- or 7-membered hydrocarbon ring containing from one to four heteroatoms selected from nitrogen, oxygen and sulfur;

Aa is a natural or synthetic amino acid;

or pharmaceutically acceptable acid addition salts, base addition salts thereof.

29. A method of killing bacteria on an inert surface or sanitizing said surface comprising applying a compound of Formula I:

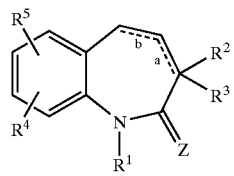

wherein:

$R^1$ is H, substituted or unsubstituted, straight chain, branched or cyclic, alkyl, alkenyl, or alkynyl, substituted or unsubstituted —Ar or —$(CH_2)_n$Ar, —$(CH_2)_m$C(=O)R, —$(CH_2)_n$CN —$(CH_2)_m$C(=Q)OR, —C(=O)N(R)$_2$, —OR, —SO$_2$R, —$(CH_2)_n$(OAr), —$(CH_2)_m$C(=NH)NH$_2$, —$(CH_2)_n$NHAr, —C(=O)N(H)(NHR), or CH$_2$(OR), wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino;

$R^2$ and $R^3$ are independently H, halogen, —N$_3$, —CN, substituted or unsubstituted, straight chain, branched or cyclic, alkyl, alkenyl, or alkynyl, substituted or unsubstituted —Ar or —$(CH_2)_n$Ar, —$(CH_2)_m$N(R)$_2$, —$(CH_2)_m$NH(Aa), —$(CH_2)_m$NC(=O)R, —$(CH_2)_m$C(=O)ONHOR, —$(CH_2)_m$C(=O)OR, —$(CH_2)_m$C(=O)NH(Aa), —$(CH_2)_m$C(=O)N(R)$_2$, or —$(CH_2)_n$C(=O)NH(Aa);

$R^4$ and $R^5$ are independently H, halogen, —NO$_2$, —CN, substituted or unsubstituted, straight chain, branched or cyclic, alkyl, alkenyl, or alkynyl, substituted or unsubstituted —Ar or —$(CH_2)_n$Ar, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino; substituted or unsubstituted primary amine or secondary amine, —NHC(=O)R, —QR, —OC(=O)N(R)$_2$, NHC(=Q)NHC(=O)OR, —NHC(=Q)NHR, —C(=O)OR, or —OSi(R)$_3$;

R is H, a substituted or unsubstituted straight chain, branched or cyclic lower alkyl, lower alkenyl or lower alkynyl, or a substituted or unsubstituted Ar or $(CH_2)_n$Ar, wherein the substituted alkyl, alkenyl or alkynyl are alkyl, alkenyl or alkynyl groups that are substituted by one, two or three F, Cl, Br, I, nitro, cyano, hydroxy, alkoxy, haloalkoxy, cyclic, branched or unbranched lower alkyl, cyclic, branched or unbranched lower alkenyl, cyclic, branched or unbranched lower alkynyl, protected hydroxy, amino, protected amino, $C_1$–$C_6$ acyloxy, carboxy, protected carboxy, carbamoyl, carbamoyloxy, or methylsulfonylamino;

Q is O or S;

Z is O or S;

a and b are a single or double bond, and when a is a double bond, only $R^2$ or $R^3$ are present;

m is 0, 1 or 2;

n is 1, 2 or 3;

Ar is aryl, arylalkyl, heterocycle, heterocyclic group, heterocyclic, heterocyclyl, or heteroaryl, wherein heterocycle, heterocyclic group, heterocyclic or heterocyclyl is any mono-, bi- or tricyclic saturated, unsaturated or aromatic ring where at least one ring is a 5-, 6- or 7-membered hydrocarbon ring containing from one to four heteroatoms selected from nitrogen, oxygen and sulfur and wherein heteroaryl is any mono-, bi- or tricyclic aromatic rings having the number of ring atoms designated where at least one ring is a 5-, 6- or 7-membered hydrocarbon ring containing from one to four heteroatoms selected from nitrogen, oxygen and sulfur;

Aa is a natural or synthetic amino acid;

or pharmaceutically acceptable acid addition salts, base addition salts thereof.

* * * * *